(12) United States Patent
Masaki et al.

(10) Patent No.: US 9,571,913 B2
(45) Date of Patent: Feb. 14, 2017

(54) SMART FLEXIBLE INTERACTIVE EARPLUG

(71) Applicant: SmartEar, Inc., San Francisco, CA (US)

(72) Inventors: Kinuko Masaki, San Francisco, CA (US); Dean Gardner, San Francisco, CA (US); Victor Valenzuela, Hayward, CA (US)

(73) Assignee: SmartEar, Inc., San Francisco, CA (US)

( * ) Notice: Subject to any disclaimer, the term of this patent is extended or adjusted under 35 U.S.C. 154(b) by 0 days.

(21) Appl. No.: 14/926,076

(22) Filed: Oct. 29, 2015

(65) Prior Publication Data

US 2016/0192050 A1 Jun. 30, 2016

Related U.S. Application Data

(60) Provisional application No. 62/072,776, filed on Oct. 30, 2014.

(51) Int. Cl.

| | |
|---|---|
| *H04R 1/10* | (2006.01) |
| *H04R 1/04* | (2006.01) |
| *H04W 4/00* | (2009.01) |
| *H04R 1/02* | (2006.01) |
| *H04R 25/00* | (2006.01) |
| *H04M 1/60* | (2006.01) |
| *H04R 3/00* | (2006.01) |
| *G10L 17/22* | (2013.01) |

(Continued)

(52) U.S. Cl.
CPC ............... *H04R 1/1016* (2013.01); *A61B 5/04* (2013.01); *A61B 5/6817* (2013.01); *G10L 17/22* (2013.01); *H04M 1/6058* (2013.01); *H04R 1/028* (2013.01); *H04R 1/04* (2013.01); *H04R 1/1041* (2013.01); *H04R 1/1058* (2013.01); *H04R 3/00* (2013.01); *H04R 25/505* (2013.01); *H04R 25/652* (2013.01); *H04W 4/008* (2013.01); *H04R 1/1083* (2013.01); *H04R 2201/103* (2013.01); *H04R 2201/107* (2013.01); *H04R 2203/00* (2013.01); *H04R 2420/07* (2013.01); *H04R 2460/11* (2013.01)

(58) Field of Classification Search
CPC ... G06F 1/1652; H04R 1/105; H04R 2430/01; G10L 2021/065; H04M 3/569
See application file for complete search history.

(56) References Cited

U.S. PATENT DOCUMENTS

| | | | |
|---|---|---|---|
| 8,389,862 B2 | 3/2013 | Arora | |
| 8,798,298 B1 * | 8/2014 | Burns | H04R 1/2876 264/267 |

(Continued)

OTHER PUBLICATIONS

International Search Report for PCT/US15/57998, and International Written Opinion for PCT/US15/57988, Apr. 29, 2016, 15 pages.

*Primary Examiner* — Bobbak Safaipour
(74) *Attorney, Agent, or Firm* — Avancept LLC; Thomas L. Ewing

(57) ABSTRACT

An embodiment of the invention provides a resiliently deformable and flexible in-ear sound device having stretchable electronic circuitry. The in-ear sound device may be configured in a variety of ways, including, but in no way limited to a smart earplug, a flexible personal sound amplification product, a personal music player, a "walkie-talkie" and the like.

53 Claims, 10 Drawing Sheets

(51) Int. Cl.
*A61B 5/04* (2006.01)
*A61B 5/00* (2006.01)

(56) References Cited

U.S. PATENT DOCUMENTS

| | | | | |
|---|---|---|---|---|
| 2002/0181336 | A1* | 12/2002 | Shields | G04F 1/005 368/109 |
| 2004/0243204 | A1* | 12/2004 | Maghribi | A61N 1/05 607/115 |
| 2008/0063231 | A1* | 3/2008 | Juneau | H04R 25/456 381/328 |
| 2009/0143096 | A1* | 6/2009 | Chang | H04M 1/6066 455/556.1 |
| 2010/0002402 | A1* | 1/2010 | Rogers | H01L 21/4867 361/749 |
| 2011/0002498 | A1 | 1/2011 | Wong | |
| 2011/0224493 | A1* | 9/2011 | Oyadiran | A61B 1/00016 600/200 |
| 2013/0142363 | A1* | 6/2013 | Amento | H04K 1/00 381/151 |
| 2014/0112520 | A1 | 4/2014 | Knudsen | |
| 2014/0169599 | A1* | 6/2014 | Solum | H04R 25/554 381/315 |
| 2014/0172042 | A1* | 6/2014 | Goorevich | H04R 25/505 607/57 |
| 2014/0301561 | A1* | 10/2014 | Silberman | H04R 1/1091 381/74 |
| 2014/0303452 | A1* | 10/2014 | Ghaffari | A61B 1/05 600/301 |
| 2015/0183167 | A1 | 7/2015 | Molinari | |

\* cited by examiner

SMART FLEXIBLE INTERACTIVE EARPLUG

FIELD

Embodiments of the invention relate to systems and methods providing in-ear sound devices. More particularly, an embodiment of the invention relates to systems and methods that use flexible electronics to provide an improved in-ear sound device.

BACKGROUND

The following description includes information that may be useful in understanding embodiments of the invention. It is not an admission that any of the information provided herein is prior art or relevant to the presently claimed invention, or that any publication specifically or implicitly referenced is prior art.

With the development of portable multimedia devices and smart phones, many types of earphones and headsets have been developed and used. However, previous devices have traditionally been bulky and uncomfortable as well as being limited in their technological abilities.

Therefore, a need exists for more advanced sound devices that can perform an expanded set of tasks at an improved rate of performance over the devices found in the prior art.

SUMMARY OF THE INVENTION

Embodiments of the invention comprise a deformable and flexible in-ear sound device. The in-ear sound device comprises a deformable and flexible body having a longitudinal axis extending between a distal end and a proximal end. The in-ear sound device further comprises an electronic component package comprising stretchable electronic circuitry. The electronic component package includes a speaker located at the distal end of the deformable and flexible body, wherein the stretchable electronic circuity is at least one of embedded in or on the deformable and flexible body. In some embodiments of the invention, the deformable and flexible body include a canal that can be opened and closed.

Embodiments of the invention further comprise a method for outputting sound to a user's ear in a deformable and flexible in-ear sound device. The method comprises placing an electronic component package comprising stretchable electronic circuitry on a deformable and flexible body having a longitudinal axis extending between a distal end and a proximal end. The stretchable electronic circuitry resides on the deformable and flexible body by at least one of embedding the electronic component package in or on the deformable and flexible body. The method further comprises placing a speaker at the distal end of the deformable and flexible body.

BRIEF DESCRIPTION OF THE DRAWINGS

Figures provided herein may or may not be provided to scale. The relative dimensions or proportions may vary. Embodiments of the invention may be sized to fit within an ear canal of a user.

DETAILED DESCRIPTION OF AN EMBODIMENT OF THE INVENTION

Figure 1:
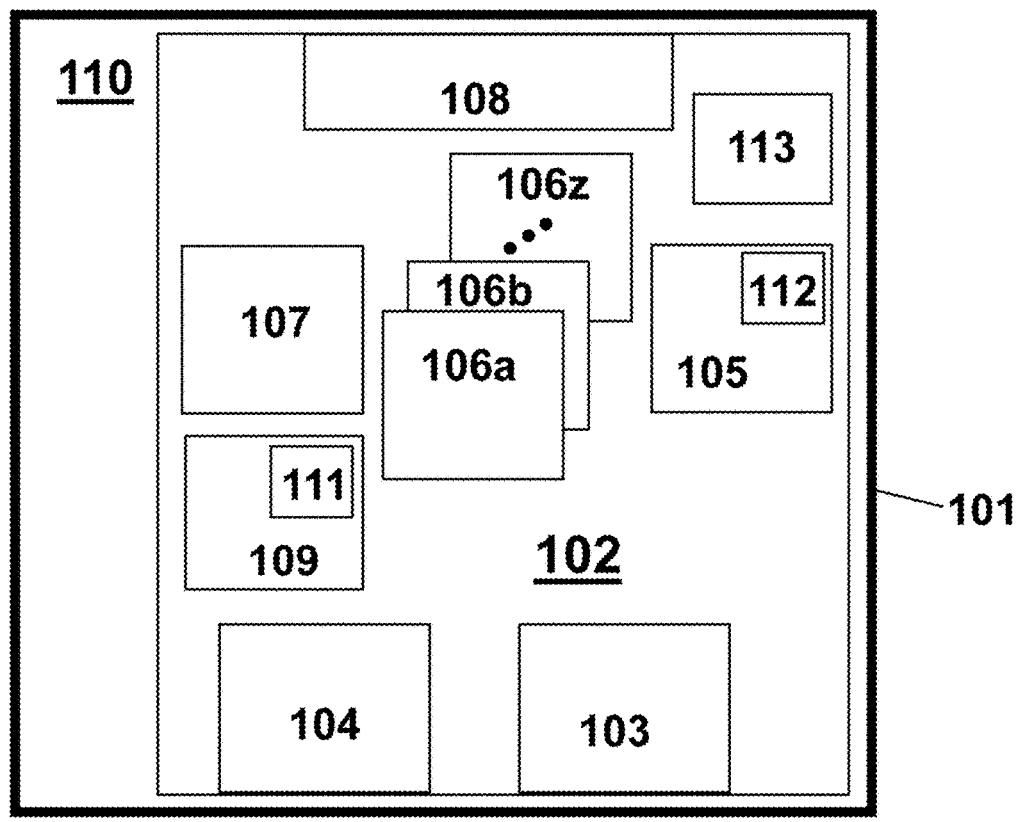
FIG. 1 provides a block diagram that illustrates an in-ear sound device 101, according to an embodiment of the invention.

Various embodiments of the invention will be described in detail with reference to the accompanying drawings. References made to particular examples and implementations are for illustrative purposes, and are not intended to limit the scope of the invention or the claims.

It should be noted that while many embodiments of the invention described herein are drawn to a smart earplug, various configurations are deemed suitable and may employ various computing devices including servers, interfaces, systems, databases, agents, engines, controllers, or other types of computing devices operating individually or collectively. One should appreciate that any referenced computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed smart earplug.

The following discussion provides many example embodiments of the claimed subject matter. Although each embodiment represents a single combination of elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C or D, even if not explicitly disclosed.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. The terms "coupled to" and "coupled with" are also used euphemistically to mean "communicatively coupled with" where two or more networked devices are able to send or receive data over a network.

Various objects, features, aspects and advantages of the claimed subject matter will become more apparent from the following detailed description, along with the accompanying drawing figures in which like numerals represent like components.

Embodiments of the invention provide a resiliently deformable and flexible in-ear sound device. The in-ear sound device may include flexible electronic components that have been manufactured on a three-dimensional printer.

Embodiments of the in-ear sound device may be used for a variety of purposes, including for use as an amplified hearing device, for use as a music player, and for use as a headphone device.

Embodiments of the invention may provide a smart earplug offering heightened sounds for a variety of uses from personal music player to "walkie-talkie." Embodiments of the invention provide an in-ear sound device that includes a wireless communications module that employs a wireless protocol so that the in-ear sound device earplug may communicate with a mobile computing device, another in-ear sound device or a remote server or network, e.g., a cloud.

Embodiments of the invention may further provide an in-ear "smartphone," e.g., a smart device having functionality rivaling that of a smartphone but using a variety of user interfaces appropriate for an aural rather than visual device, including but not limited to voice recognition technology. The "smartphone" embodiment of the in-ear sound device may also include a visual user interface operating on some form of computing platform, according to an embodiment of the invention.

Electronic component packages used in embodiments of the in-ear sound device may comprise flexible electronic components as, for example, small nano-electronic devices. Electronic components may include a microphone, an amplifier, a battery, a speaker, a wireless communications module, and/or any combination thereof. The electronic component package in some embodiments may include a processor and/or a data storage component. For example, the electronic component may include functionality for executing any number of software applications ("apps") and/or storing data such as media.

FIG. 1 provides a block diagram that illustrates an in-ear sound device 101, according to an embodiment of the invention. The in-ear sound device 101 is formed of a deformable and flexible body 110 that contains an electronic component package 102. The electronic component package 102 is embedded in or on the deformable body 110 and includes electronic circuitry for the in-ear sound device 101. The specific configuration of the electronic component package 102 may vary from embodiment to embodiment of the in-ear sound device 101.

The deformable body 110 allows the in-ear sound device 101 to be inserted into a user's ear canal without damaging the in-ear sound device 101 or causing harm to the subject's ear. In various embodiments, the electronic component package 102 may be impregnated within the body 110 of the in-ear sound device 101, disposed on a surface of the body 110, encased within the body 110, and/or various other combinations of dispositions. The resiliently deformable material used to form body 110 allows the in-ear sound device 101 to be a "one size fits all" and conform to a broad range of ear canal anatomies.

The electronic component package 102 may include one or more electronic components such as a microphone 103, a wireless communications module 104, an amplifier 105, a battery 113, a processor 107, a speaker 108, and a data storage component 109, according to an embodiment of the invention. The individual components in the electronic component package 102 may be electrically coupled and/or wired as needed for conventional functionality of such components. Along with the body 110, the electronic component package 102 may also be deformable in some embodiments of the invention.

Embodiments of the in-ear sound device 101 may include a microphone 103 that communicates with a speaker 108. The microphone 103 may be in electronic and/or mechanical communication with the speaker 108. Sound/vibrations picked up by the microphone 103 may be transmitted to the speaker 108. In some embodiments, the sound/vibrations picked up may be amplified via the amplifier 105 and transmitted to the speaker 108. In various embodiments, the amplifier 105 includes a digital signal processor (DSP) 112.

Figure 11:
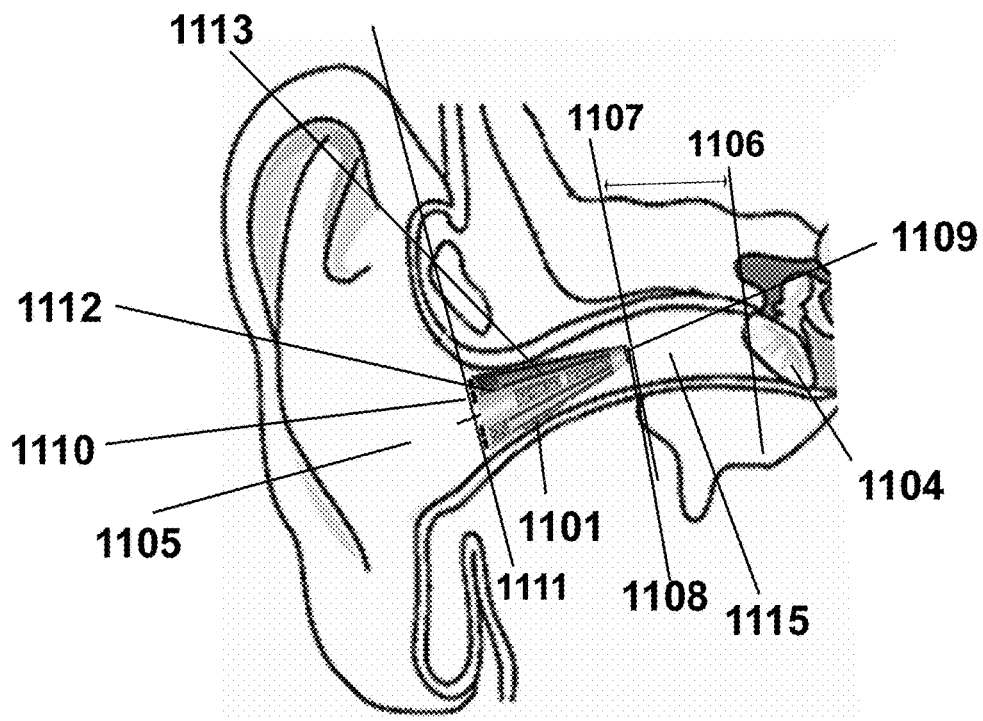
FIG. 11 illustrates an in-ear sound device 1101 inserted into an ear 1105, according to an embodiment of the invention.

The speaker 108 may be closer to the eardrum than the microphone 103 during operation. (As shown in FIG. 11, a speaker 1108 is disposed at the distal tip 1107 of the body of the in-ear sound device 1101 while a microphone 1110 is disposed in the proximal portion 1111 of the in-ear sound device 1101). In some embodiments, the speaker 108 may contact the eardrum or be in even closer proximity to the ear drum than indicated in FIG. 1. The microphone 103 may be external to the ear, or closer to ear canal opening.

In some embodiments, the in-ear sound device 101 itself may be on the order of about 1 mm-5 cm in length. In some embodiments, the distance between the speaker 108 and the microphone 103 may be at a distance between from 1 mm to 5 cm. As a general matter, the greater the distance is between the microphone 103 and the speaker 108, then there is lower likelihood of feedback issues between the microphone 103 and the speaker 108.

However, in some embodiments, the dimensions of the in-ear sound device 101 and/or the distance between the microphone 103 and the speaker 108 might be smaller and/or larger than the dimensions/distances provided above. For example, an embodiment of the invention may be prepared for users wearing helmets (e.g., as police officers, soldiers, football players, motorcyclists, and/or bicyclists). Similarly, an embodiment of the in-ear sound device made for security personnel, hunters, etc. might be extended in size to accommodate additional microphones, or higher fidelity microphones, and/or enhanced communications equipment.

In embodiments, audio input to the speaker 108 may come from the wireless communications module 104, for example when the wireless communications module 104 is configured for Bluetooth®. Additionally, audio input to the speaker 108 may come from the data storage component 109 of the in-ear sound device 101.

In embodiments, the in-ear sound device 101 further includes a processor 107 which may be integral with the electronic component package 102 or operate under the control of a computing device (e.g., a mobile computing device) sending instructions via the communications module 104.

The processor 107 in the in-ear sound device 101 may execute software applications 111, an embodiment of the invention. The software applications 111 may either be stored in the data storage component 109 or delivered to the processor 107 via the communications module 104 from a remote storage device located away from the in-ear sound device 101. For example, the processor 107 might execute a software application that resides on a mobile phone linked to the in-ear sound device 101. A skilled artisan will appreciate that many software applications known in the art may be utilized.

The processor 107 may be configured with processor-executable instructions 111 to perform operations to distinguish meaningful sound, such as speech, from ambient noise. Such instructions may perform operations for receiving sound signals from the microphone 103, such as determining whether the sound signals represent meaningful sound, activating the speaker 108 when the sound signals represent meaningful sound, and deactivating the speaker 108 when the sound signals do not represent meaningful sound. Such instructions 111 for a speech detection program may be present in a memory component 109 of the in-ear sound device 101 or a coupled mobile computing device.

The processor 107 may comprise a CPU or like computing device or may alternatively comprise a simple circuit that directs the operations of the various components in the electronic component package 102, according to an embodiment of the invention. In embodiments in which the processor 107 comprises a simple control circuit, the other components in the electronic component package 102 may also be simple and/or few in number, e.g., just a battery 113, a data storage component 109, and a speaker 108, in addition to the processor 107.

The data storage component 109 may comprise a non-transitory memory, such as RAM, flash, ROM, hard drive, solid state, drive, optical media and the like. The data storage component 109 may include various types of data, such as media, music, software, and the like.

The wireless communications module 104 can be implemented using a combination of hardware (e.g., driver circuits, antennas, modulators/demodulators, encoders/decoders, and other analog and/or digital signal processing circuits) and software components. Multiple different wireless communication protocols and associated hardware can be incorporated into the wireless communications module 104.

The wireless communications module 104 includes structural and functional components known in the art to facilitate wireless communication with another computing device or remote network. The wireless communications module 104 can include RF transceiver components such as an antenna and supporting circuitry to enable data communication over a wireless medium, e.g., using Wi-Fi (IEEE 802.11 family standards), Bluetooth® (a family of standards promulgated by Bluetooth SIG, Inc.), or other protocols for wireless data communication. In some embodiments, wireless communications module 104 can implement a short-range sensor (e.g., Bluetooth, BLTE or ultra-wide band).

In some embodiments, the wireless communications module 104 can provide near-field communication ("NFC") capability, e.g., implementing the ISO/IEC 18092 standards or the like. NFC can support wireless data exchange between devices over a very short range (e.g., 20 centimeters or less). NFC typically involves a near field magnetic induction communication system that provides a short range wireless physical layer that communicates by coupling a tight, low-power, non-propagating magnetic field between devices. In such embodiments, the wireless communication module 104 may include a transmitter coil in the in-ear sound device 101 to modulate a magnetic field which is measured by means of a receiver coil in another device, e.g., another in-hear sound device or a smartphone.

In some embodiments of the invention, the in-ear sound device 101 can communicate bi-directionally via a network. In such embodiments, the wireless communications module 104 may comprise a Bluetooth® digital wireless protocol such that the in-ear sound device 101 may communicate with a mobile computing device. Bluetooth® technology provides a low-cost communication link. The Bluetooth® transceiver in an embodiment of the wireless communications module 104 may be configured to establish a wireless data link with a suitably equipped mobile computing device and/or another in-ear sound device.

In an embodiment, the communications module 104 of the in-ear sound device 101 may operate in conjunction with another in-ear sound device (e.g. one in-ear sound device in a left ear and another in-ear sound device in a right ear), while in another embodiment an in-ear sound device 101 may operate independently. In yet another embodiment, at least one in-ear sound device 101 may operate in conjunction with a mobile computing device.

The in-ear sound device 101 may operate as a walkie-talkie device communicating with another in-ear sound device operating in another ear of the user, with another device associated with the user, with another in-ear sound device associated with another user, and/or with a third-party device. In some embodiments, a user of the in-ear sound device 101 might be able to communicate with another in-ear sound device user using little more than just a whisper and at great distances.

The in-ear sound device 101 may also include functionality to communicate bi-directionally via a long-range wireless network. In one embodiment, the long-range wireless network includes a cellular network. In another embodiment, the long-range wireless network includes a multimedia communications network. In another embodiment, the long-range wireless network includes wireless technologies such as Global System for Mobile Communications (GSM), Code Division Multiple Access-One (cdmaOne), Time Division Multiple Access (TDMA), PDC, Japan Digital Cellular (JDC), Universal Mobile Telecommunications System (UMTS), Code Division Multiple Access-2000 (cdma2000), and Digital Enhanced Cordless Telephony (DECT).

Embodiments of the in-ear sound device 101 may also include a wireless communications module 104 configured to communicate with a remote server or network. In one embodiment, the remote network is a cloud computing platform.

As used herein, the term "mobile computing device" refers to anyone or all of cellular telephones, tablet computers, phablet computers, personal data assistants (PDAs), palm-top computers, notebook computers, laptop computers, personal computers, wireless electronic mail receivers and cellular telephone receivers (e.g., the Blackberry® and Treo® devices), multimedia Internet enabled cellular telephones (e.g., Blackberry Storm®), multimedia enabled smart phones (e.g., Android® and Apple iPhone®), and similar electronic devices that include a programmable processor, memory, a communication transceiver, and a display.

In embodiments, the in-ear sound device 101 may include one or more sensors 106a-106z configured to detect and/or measure various phenomenon. In one embodiment, the in-ear sound device 101 may include one or more sensors 106a-106z configured to detect a physiological parameter of the user. Physiological parameters detected or measured by the sensors 106a-106z may include body temperature, pulse, heart rate, $VO_2$ Max (also known as maximal oxygen consumption), pulse oximetry data, respiratory rate, respiratory volume, maximum oxygen consumption, cardiac efficiency, heart rate variability, metabolic rate, blood pressure, EEG data, galvanic skin response data, and/or EKG/ECG. Thus, the sensors 106a-106z may detect, for example, the ambient temperature, humidity, motion, GPS/location, pressure, altitude and blood analytes such as glucose of the user of the in-ear sound device.

In an embodiment, the in-ear sound device 101 may include one or more sensors 106a-106z configured to detect the location or motion of the user, such as, for example an accelerometer, a GPS sensor, a gyroscope, a magnetometer, and/or radiometer. In an embodiment, the in-ear sound device 101 may include a voice sensor 106a coupled to the microphone 103.

Specific sensor 106a-106z configurations may vary across embodiments of the in-ear sound device 101, e.g., one embodiment might include an ambient temperature sensor, a heart rate sensor, and a motion sensor while another embodiment includes a pressure sensor, a pulse sensor, and a GPS locator.

In another embodiment, the in-ear sound device 101 may provide various alarm and notification functions. For example, the in-ear sound device 101 may be utilized as an alarm clock. This functionality could be provided by the processor 107 and/or the processor 107 coupled with the data storage device 109 and/or the processor 107 coupled with the communications module 104 and a third device (e.g., a mobile phone). An ordinary artisan should know how to make the processor 107 may provide an alarm function. In addition, the processor 107 in conjunction, for example, with data stored in the data storage component 109 may provide a calendar function, a timer function, a stopwatch function, and/or a reminder function. Similarly, the processor 107 in combination with data 111 from the data storage component 109 combined with data from various sensors 106a-106z may provide various alarm and/or warning functions, e.g., a heart attack warning or a high blood pressure warning. Similarly, in conjunction with the communications module 104 and the sensors 106a-106z could provide various alarms to various third parties remote from the in-ear sound device 101. For example, if the in-ear sound device 101 was equipped with one or more accelerometer 106a, then a third party could be automatically notified of an event such as a car crash, a bicycle crash, and/or a fall.

The in-ear sound device 101 can also be configured to provide various forms of authentication. For example, the microphone 103 in combination with the DSP 112, the processor 107, and the data storage component 109 using voice data 111 can be used to provide authentication of the authorized user(s) of the in-ear sound device 101. This electrical component combination could be used to determine when the in-ear sound device 101 has been stolen or otherwise being operated by an unauthorized person. As mentioned above, the processor 107 could be a simple control circuit configured for the authentication function rather than a processor chip configured to control the authentication function. The authentication function could also be used to verify the user before delivering sensitive information through the speaker 108.

The authentication function could be provided in a number of ways, including but not limited to a voice recognition process known in the art. As disclosed in FIG. 11, embodiments of the in-ear sound device 1101 include a speaker 1108 disposed at the distal tip 1107 of the body 1112 of the in-ear sound device 1101 and a microphone 1110 disposed in the proximal portion 1111 of the in-ear sound device 1101. The processor 107 (possibly in conjunction with the DSP 112) can analyze a received sample of the user's voice.

In an alternative embodiment, authentication may be performed outside the in-ear sound device 101 via a device such as a smartphone. In such an embodiment, the in-ear sound device 101 only needs the microphone 103 and the communications module 104 to perform the authentication function.

A user interface for the electronic component package 102, including the sensors 106a-106z, could be provided to the user via the wireless communications module 104 and another device such as a mobile phone or a computer, according to an embodiment of the invention. A voice command user interface could also be provided via the microphone 103 and the processor 107, according to an embodiment of the invention. An ordinary artisan should know how to configure such a user interface.

Sensors, and combinations of sensors 106a-106z, may also be used to provide a user interface function. For example, an accelerometer (or a G-force sensor) might activate when a user moves his/her hand near the G-force sensor and provides a certain G-force (e.g., 1G/2G/3G) this action could trigger the sensor such that additional commands might be received through additional actions such as further tapping. For example, a user might tap his/her jaw, ear, check, neck, or another pre-designated location (e.g., via a predesignated single tap, double tap, or triple tap). This tapping action could trigger the sensor such that additional commands could be received through tapping. So, for example, once the G-force sensor has been activated, then two more taps might activate a music player. The user's selection could be confirmed by appropriate auditory confirmation delivered through the speaker 108. Choices made by the user as well as possible command selections could be spoken to the user via the speaker 108. Similar sensor configurations could also be used for user input functions, such as accelerometers, pulse rate, and temperature sensors.

The in-ear sound device 101 described herein may be waterproof and worn in many situations, such as during swimming or while bathing. The in-ear sound device 101 may also be worn during sleep without discomfort. This may allow the in-ear sound device 101 to be utilized during many times when conventional sound devices may be uncomfortable, simply not work, or even be dangerous to use.

Figure 2:
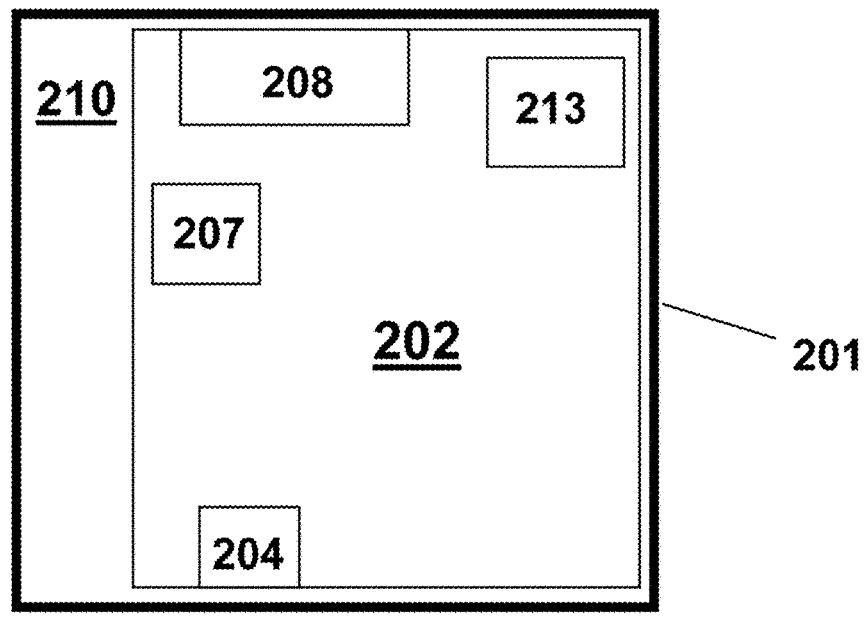
FIG. 2 illustrates an embodiment of an in-ear sound device 201 configured to function as a headphone, according to an embodiment of the invention.

FIG. 2 illustrates an embodiment of an in-ear sound device 201 configured to function as a headphone, according to an embodiment of the invention.

The in-ear sound device 201 comprises a speaker 208, a battery 213, a communication module 204, and a control circuit 207 in an electronic component package 202. The in-ear sound device 201 may comprise additional electronic components in the headphone embodiment. The electronic component package 202 is placed in or on a deformable body 210.

The control circuit 207 may operate in a conventional manner for such circuits, controlling the receipt of data (e.g., music or voice data) from outside the in-ear sound device 201 via the communication module 204 and transferring the data to the speaker 208, with operations powered by the battery 213. The control circuit 207 may in some embodiments comprise a dedicated computer chip (or processor) configured to provide equivalent or superior functionality to a control circuit, according to an embodiment of the invention.

Figure 3:
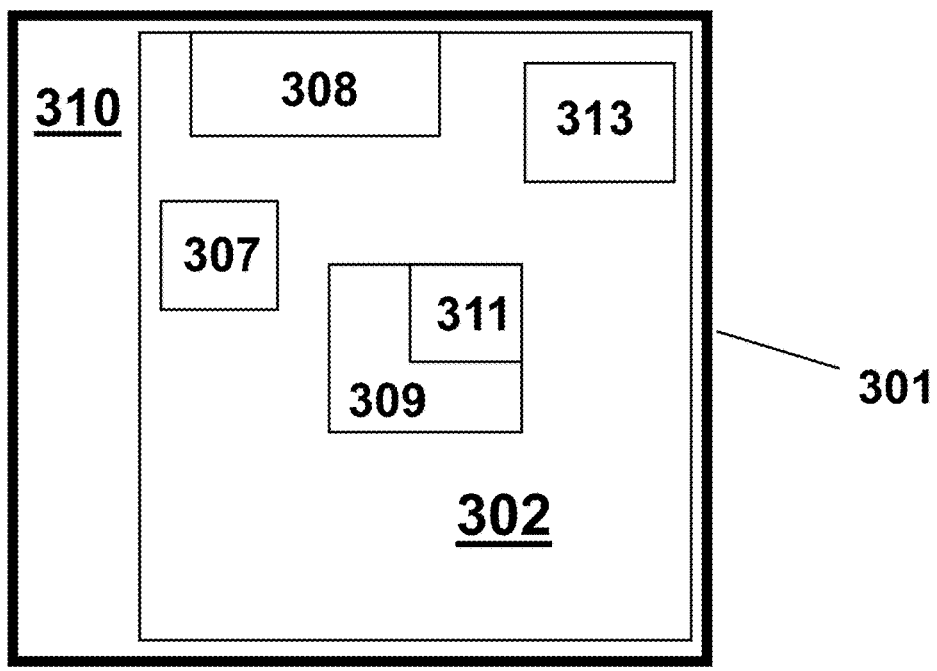
FIG. 3 illustrates an embodiment of an in-ear sound device 301 configured to function as a music player, according to an embodiment of the invention.

FIG. 3 illustrates an embodiment of an in-ear sound device 301 configured to function as a music player, according to an embodiment of the invention.

The in-ear sound device 301 comprises a speaker 308, a battery 313, a data storage component 309, and a control circuit 307 in an electronic component package 302. The in-ear sound device 301 may comprise additional electronic components in the music player embodiment. The data storage component 309 includes music data 311. The electronic component package 302 is placed in or on a deformable body 310.

The control circuit 307 may operate in a conventional manner for such circuits, obtaining music data 311 from the data storage component 309 and directing transfer of the music data 311 to the speaker 308, with operations powered by the battery 313. The control circuit 307 may in some embodiments comprise a dedicated computer chip (or processor) configured to provide equivalent or superior functionality to a control circuit, according to an embodiment of the invention.

Figure 4:
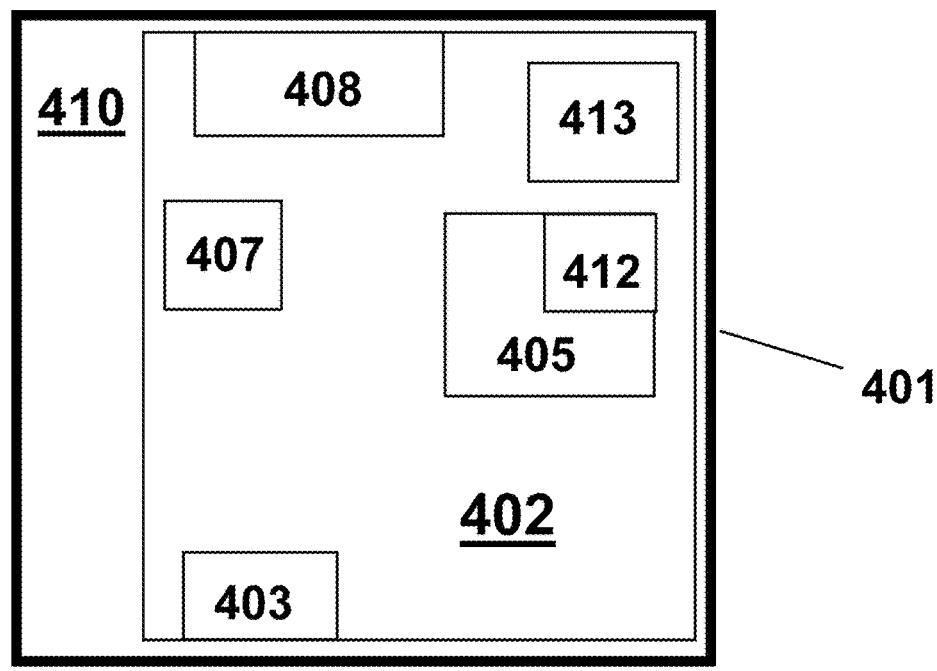
FIG. 4 illustrates an embodiment of an in-ear sound device 401 configured to provide hearing amplification, according to an embodiment of the invention.

FIG. 4 illustrates an embodiment of an in-ear sound device 401 configured to provide hearing amplification, according to an embodiment of the invention.

The in-ear sound device 401 comprises a speaker 408, a battery 413, a microphone 403, an amplifier 405, and a control circuit 407 in an electronic component package 402. The in-ear sound device 401 may comprise additional electronic components in the hearing amplification embodiment, such as a digital signal processor (DSP) 412. The electronic component package 402 is placed in or on a deformable body 410.

The control circuit 407 may operate in a conventional manner for such circuits, receiving sound data from the microphone 403, directing transfer of the data to the amplifier 405 (and possibly the DSP 412), and then on to the speaker 408, with operations powered by the battery 413. The control circuit 407 may in some embodiments comprise a dedicated computer chip (or processor) configured to provide equivalent or superior functionality to a control circuit, according to an embodiment of the invention. In some embodiments, the control circuit 407 may also direct the operations of the DSP 412.

Figure 5:
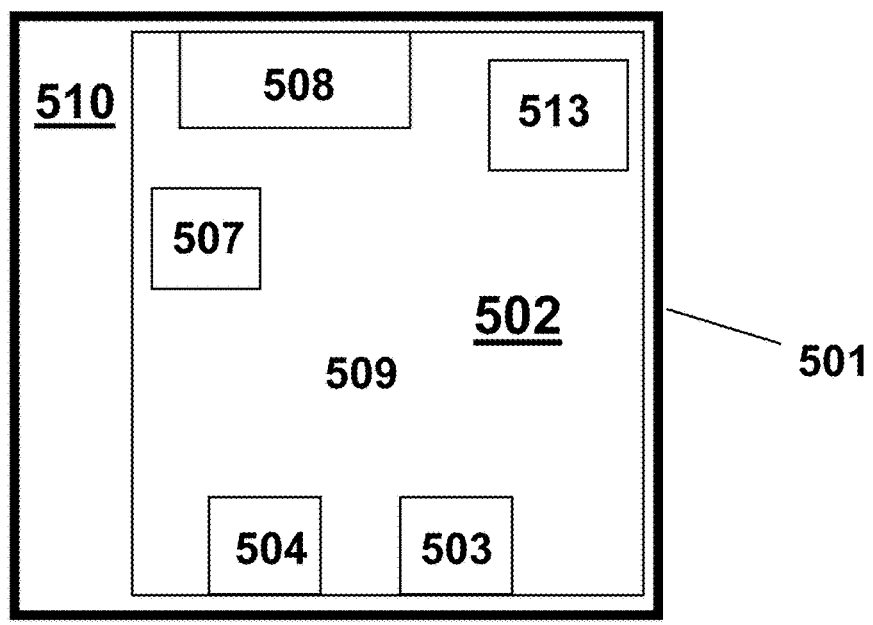
FIG. 5 illustrates an embodiment of an in-ear sound device 501 configured to provide a walkie-talkie function (a portable, two-way radio transceiver), according to an embodiment of the invention.

FIG. 5 illustrates an embodiment of an in-ear sound device 501 configured to provide a walkie-talkie function (a portable, two-way radio transceiver), according to an embodiment of the invention.

The in-ear sound device 501 comprises a speaker 508, a battery 513, a microphone 503, a communication module 504, and a control circuit 507 in an electronic component package 502. The in-ear sound device 501 may comprise additional electronic components in the walkie-talkie embodiment. The electronic component package 502 is placed in or on a deformable body 510.

The control circuit 507 may operate in a conventional manner for such circuits, receiving sound data from the microphone 503, directing transfer of the data to the speaker 508, with operations powered by the battery 513. The control circuit 507 may in some embodiments comprise a dedicated computer chip (or processor) configured to provide equivalent or superior functionality to a control circuit, according to an embodiment of the invention.

Figure 6:
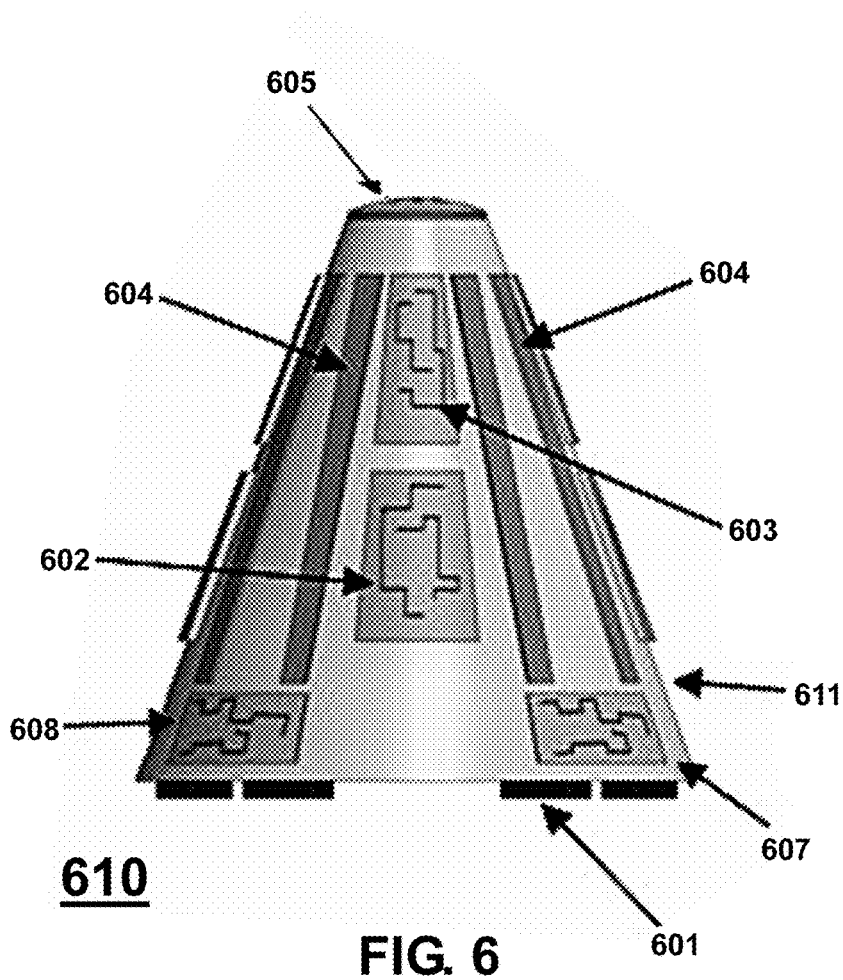
FIG. 6 illustrates an embodiment of an in-ear sound device 610 that employs stretchable circuitry in the electronic component package 611 of the in-ear sound device 610.

FIG. 6 illustrates an embodiment of an in-ear sound device 610 that employs stretchable circuitry in the electronic component package 611 of the in-ear sound device 610. The electronic component package 611 of the in-ear sound device 610 is embedded in or on a resiliently deformable body 607 and includes stretchable electronic circuitry allowing the in-ear sound device 610 to be inserted into a subject's ear canal without damaging the in-ear sound device 610 or harming the user's ear.

In various embodiments, the electronic component package 611 may be impregnated within the body 607 of the in-ear sound device 610, disposed on a surface of the body 607, encased within the body 607, and/or various combinations of dispositions.

Stretchable electronic circuitry in the electronic component package 611 may comprise an elastomeric substrate such that when it is stretched the components separate relative to each other. In other words, a speaker 605 may become relatively farther away from a microphone 601, according to an embodiment of the invention. When the electronic components are stretched, the electrical interconnection maintains substantially identical electrical performance characteristics. The electrical interconnections are sufficiently elastic such that the stretching may extend the separation distance between the electrical components to many times that of the unstretched distance without degradation of performance for the in-ear sound device 610.

The in-ear sound device 610 includes a microphone 601, a wireless communications module 602, an amplifier 603, a battery 604, and speaker 605. The in-ear sound device 610 may include other components and sensors, such as the components and sensors shown and described with respect to FIG. 1, according to an embodiment of the invention. The in-ear sound device 610 may include additional components of the same type, e.g., multiple batteries 604.

In some embodiments of the invention, sub-components of the electronic component of the in-ear sound device 610 are stretchable, e.g., microphone 601, amplifier 603, battery 604, speaker 605, and wireless communications module 602. In some embodiments of the invention, the electronic component package 611 may include one or more stretchable components in combination with non-stretchable, traditional components.

Figure 7:
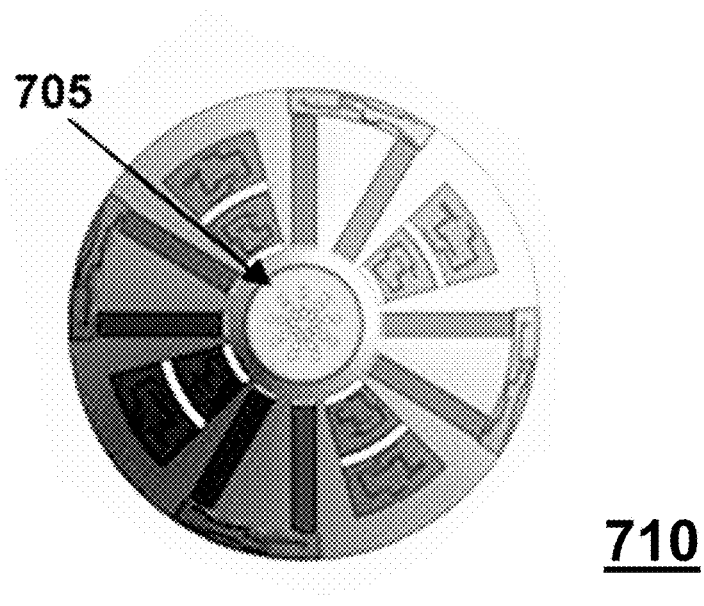
FIG. 7 illustrates an in-ear sound device 710, according to an embodiment of the invention.

FIG. 7 illustrates an in-ear sound device 710, according to an embodiment of the invention. The in-ear sound device 710 includes a speaker 705 at its proximal tip as shown in FIG. 7, according to an embodiment of the invention. The in-ear sound device 710 otherwise functions in a manner similar to the in-ear sound device 610 shown in FIG. 6 and may contain additional components such as those shown in FIG. 1.

Figure 8:
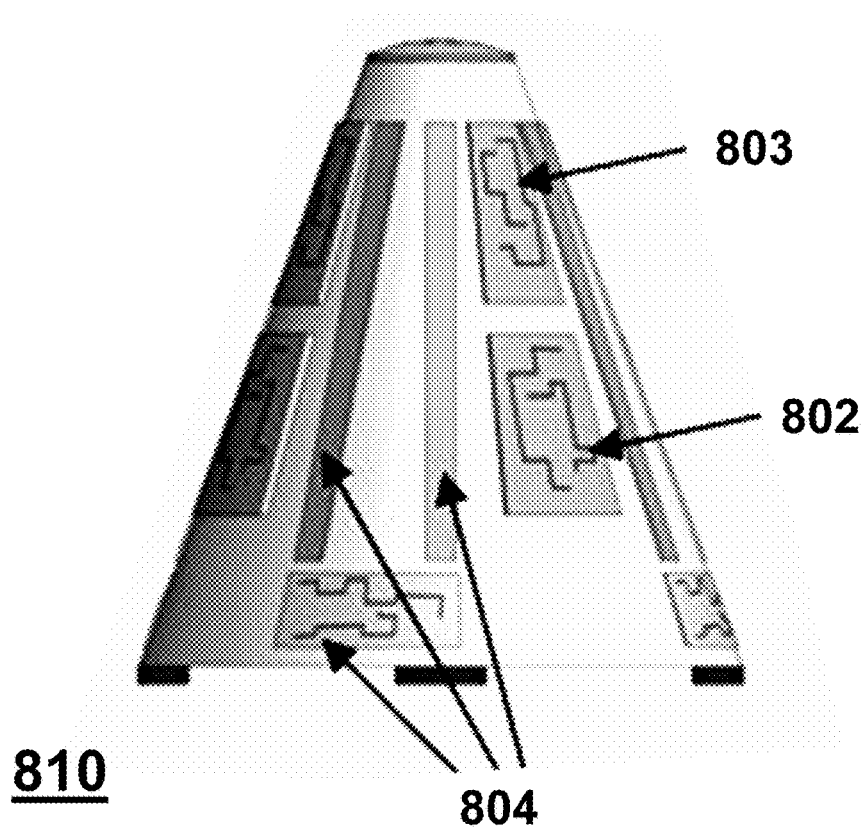
FIG. 8 illustrates an in-ear sound device 810, according to an embodiment of the invention.

FIG. 8 illustrates an in-ear sound device 810, according to an embodiment of the invention. The in-ear sound device 810 includes a number of batteries 804, a wireless communications module 802, and an amplifier 803, according to an embodiment of the invention. The in-ear sound device 810 otherwise functions in a manner similar to the in-ear sound device 610 shown in FIG. 6 and may contain additional components such as those shown in FIG. 1.

Figure 9:
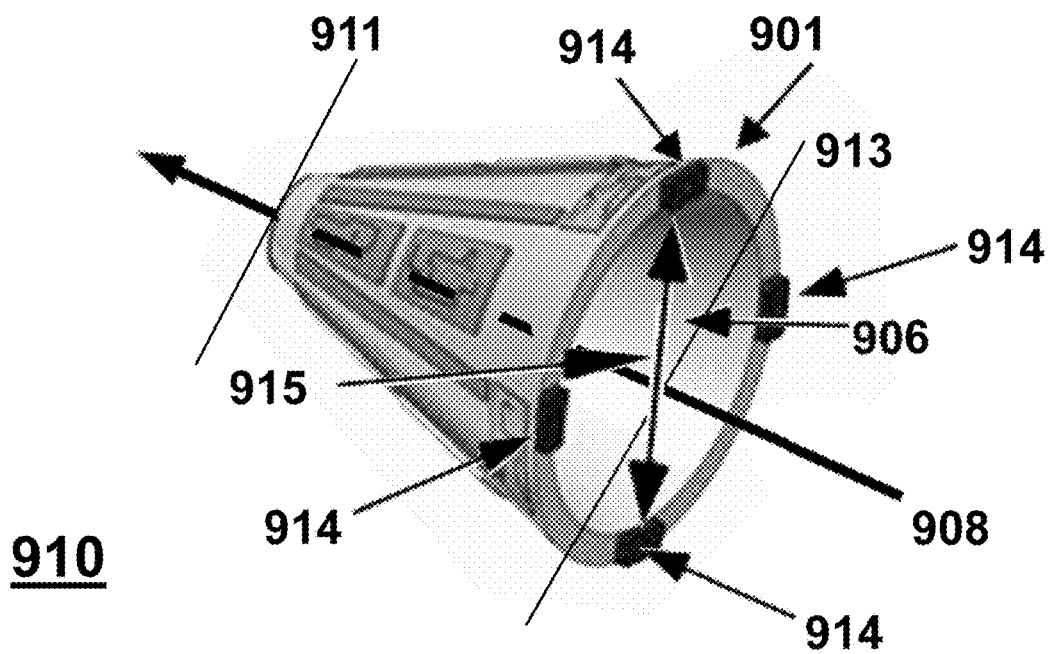
FIG. 9 illustrates an in-ear sound device 910 having a hole or canal 906 running along its longitudinal axis 908, according to an embodiment of the invention.

FIG. 9 illustrates an in-ear sound device 910 having a hole or canal 906 running along its longitudinal axis 908, according to an embodiment of the invention. The canal 906 extends along the longitudinal axis 908 of a body 901 from the distal region 913 to the proximal region 911.

Figure 12:
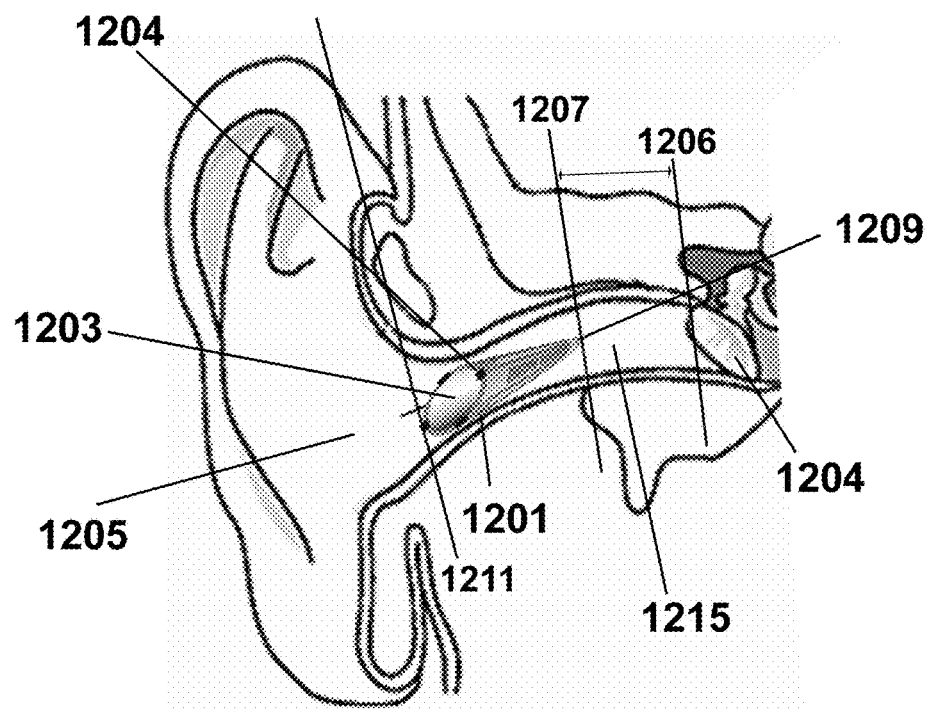
FIG. 12 illustrates an in-ear sound device 1201 inserted into an ear 1205, according to an embodiment of the invention.

Closure of the canal 906 occludes or filters out ambient sound while opening the canal 906 allows outside sound into the ear canal, e.g., the ear canal 1215 shown in FIG. 12. As such, the in-ear sound device 910 may provide the user with variable occlusion.

Having the canal 906 open provides a venting function that reduces dangerous back pressure in the ear canal (e.g., the ear canal 1215 shown in FIG. 12). Having the canal 906 open also reduces the occlusion effect which occurs when an object fills the outer portion of an ear canal giving the user a perception of a hollow or booming echo-like sound for the user's own voice. Thus, opening the canal 906 also facilitates conventional voice communications for the user of the in-ear sound device 910 with other persons, e.g., a flight attendant in an airplane when the wearer of the in-ear sound device 910 is otherwise listening to music. In addition, having the canal 906 open also makes the in-ear sound device 910 fit tighter in the user's ear, which may be helpful during activities such as exercise when the in-ear sound device 910 might be more prone to falling out.

Having the canal 906 closed improves the sound quality delivered to the user's ear. Having the canal 906 closed may also (and/or alternatively) provide additional noise cancellation that improves the quality of the sound delivered to the user's ear. Having the canal 906 closed may also (and/or alternatively) protect a user of the in-ear sound device 910 from very loud sounds and therefore protect the user's hearing. Some users may have the canal 906 in a closed or nearly closed position at all times in order to have the highest possible sound quality delivered to their ear drum, e.g., the ear drum 1204 shown in FIG. 12.

Accordingly, the in-ear sound device 910 may include functionality, such as clamps 914 that can be used to vary the diameter 915 of the canal 906 allowing for the level of occlusion of the ear canal (e.g., the ear canal 1215 shown in FIG. 12) to be adjusted, according to an embodiment of the invention. The clamps 914 may be integral to the in-ear sound device 910 or may be coupled to the in-ear sound device 910, according to an embodiment of the invention. The in-ear sound device 910 may include more or fewer claims 914 than the four clamps 914 shown in FIG. 9.

The level of occlusion of the user's ear may be adjusted/actuated by input from the user (by hand) or automatically by the user or by a program using an actuator in the clamp 914 in communication with the other components of the in-ear sound device 910, such as a processor and a battery (e.g., the processor 107 and the battery 113 shown in FIG. 1). An ordinary artisan should be capable of designing an appropriate mechanism for opening and closing the canal 906 of the in-ear sound device 910.

In some embodiments, the clamps 914 may be actuated by a touch and/or voice command, depending on the electronic component package (e.g., the electronic component package 101 shown in FIG. 1) provided to the in-ear sound device 910.

There are several alternative means for controlling the opening and closing of the canal 906 apart from the clamps 914. Alternative means for closing the canal 906 include pressure pumps, thermodynamic means by adjusting temperature, via chemical means, and via electronic means.

Figure 10:
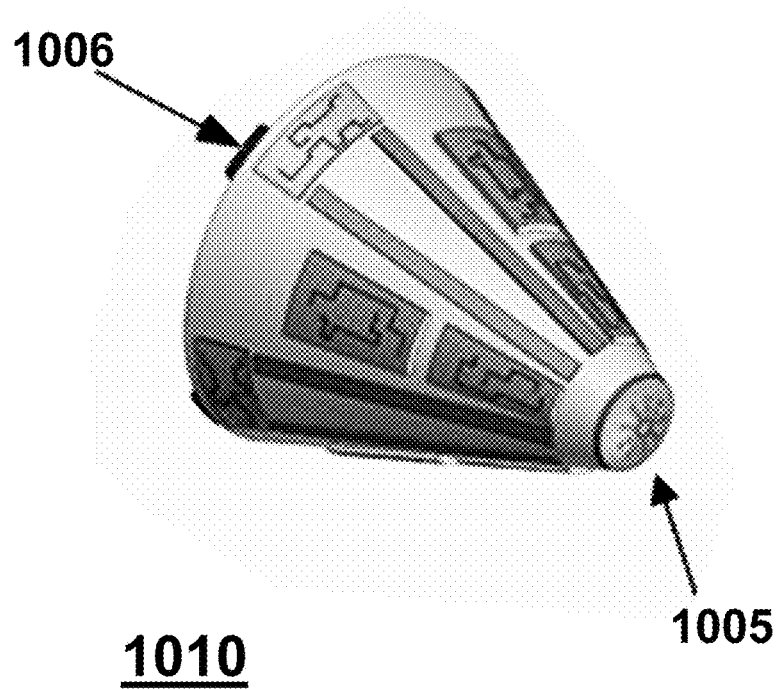
FIG. 10 illustrates an in-ear sound device 1010 having a microphone 1005 at its proximal tip and at least one clamp 1006 for closing a canal (e.g., the canal 906 shown in FIG. 9) in the in-ear sound device 1010, according to an embodiment of the invention.

FIG. 10 illustrates an in-ear sound device 1010 having a microphone 1005 at its proximal tip and at least one clamp 1006 for closing a canal (e.g., the canal 906 shown in FIG. 9) in the in-ear sound device 1010, according to an embodiment of the invention. The in-ear sound device 1010 otherwise resembles the in-ear sound device 910 shown in FIG. 9 and may have an electronic component package similar to the electronic component package 102 shown in FIG. 1, according to an embodiment of the invention.

FIG. 11 illustrates an in-ear sound device 1101 inserted into an ear 1105, according to an embodiment of the invention. The in-ear sound device 1101 includes a flexible electronics package, such as shown in the in-ear sound device 610 shown in FIG. 6 and/or the electronics component package 102 shown in FIG. 1. Embodiments of the in-ear sound device 1101 include a speaker 1108 disposed at the distal tip 1107 of the body of the in-ear sound device 1101 and a microphone 1110 disposed in the proximal portion 1111 of the in-ear sound device 1101.

The in-ear sound device 1101 comprises a deformable and flexible body 1112 having a longitudinal axis 1109 extending between a distal end 1111 and a proximal end 1107. The distal end 1111 resides just outside the ear 1105 so that the in-ear sound device 1101 may be easily removed, according to an embodiment of the invention.

Embodiments of the invention provide an in-ear sound device 1101 composed of a deformable and flexible material that is comfortable to wear for a long period of time and can be produced in bulk eliminating the need for customization. An electronic component package 1113 is embedded in or on the deformable body of the in-ear sound device 1101 and includes electronic circuitry allowing the in-ear sound device 1101 to be inserted into the user's ear canal 1115 without damaging the in-ear sound device 1101 or causing injury to the user's ear 1105, according to an embodiment of the invention. The electronic component package 1113 may be embedded in the flexible body 1112, wrapped around the flexible body 1112, and/or pressed into the flexible body 1112.

In practical application, the in-ear sound device 1101 is "squished" between the fingers of the user and inserted into the ear canal 1115 where it expands to conform to the shape of the ear canal 1115.

In some embodiments, the in-ear sound device 1101 may be returned to a "squished" position before removing the in-ear sound device 1101 from the ear canal 1115. This may allow the in-ear sound device 1101 to slide out of the ear 1105 for easy removal. In other embodiments, the in-ear sound device 1101 may be in an expanded position, or may be in some intermediate position while the in-ear sound device 1101 is removed from the ear canal.

Embodiments of the deformable body 1112 can be fabricated from many resilient polymeric materials known in the art. There are many known resilient polymeric materials that may be used to form in-ear sound devices, such as the in-ear sound device 1101. For example, natural rubber, neoprene rubber, SBR rubber (styrene block copolymer compounds), silicone rubber, EPDM rubber, polybutadiene rubber, polyvinylchloride elastomers, polyurethane elastomers, ethylene vinyls, acetate elastomers, elastomers based on acrylic acid precursors and vinyhalide polymers may all be generally suitable materials which can be used to provide the necessary Shore A Durometer values.

In some embodiments of the invention, the deformable body 1112 of the in-ear sound device 1101 is formed of material that has a Shore A Durometer hardness value (by the technique of ASTM 2240-81) of between about 10 and 30 or between 15 and 25.

Figure 18:
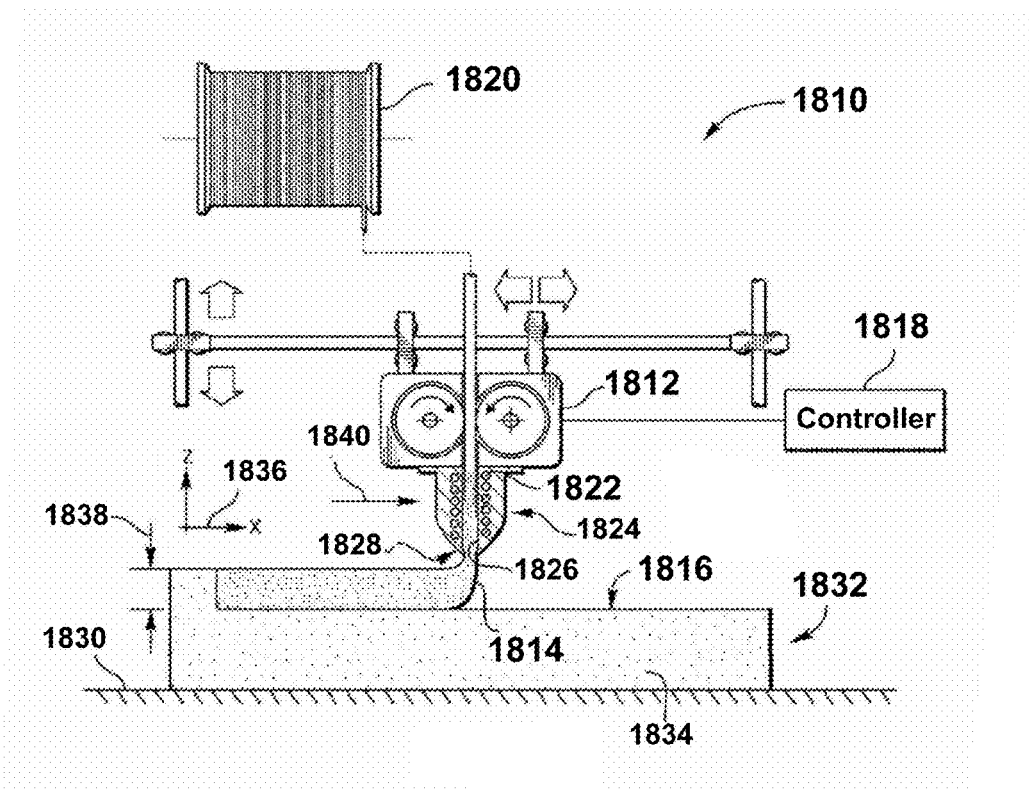
FIG. 18 illustrates a three-dimensional (3D) printer 1810 that may form an in-ear sound device 1832, according to an embodiment of the invention.

The in-ear sound device 1101 may be manufactured by 3D printing in some embodiments, using, for example, a printing apparatus such the 3D printer 1810 shown in further detail in FIG. 18. The ear plug portion of the device (e.g., the body 1112) as well as the electronics component package 1113 of the in-ear sound device 1101 are amenable to manufacturer by 3D printing. A few components such as the speaker (e.g., the speaker 108 shown in FIG. 1) may need to be added to the device 1101 at the end of the manufacturing process since speakers at the moment require post manufacturing tuning that might not yet be possible with some 3D printing machines.

FIG. 11 illustrates an in-ear sound device 1101 inserted into a human ear 1105. Embodiments of the in-ear sound device 1101 may be configured for non-human ears, such as other primates, other mammals, and even non-mammalian species. Components of the electronics component package and the elastic body would be sized accordingly in these embodiments of the invention.

FIG. 12 illustrates an in-ear sound device 1201 inserted into an ear 1205, according to an embodiment of the invention. The in-ear sound device 1201 includes a flexible electronics package such as shown in the in-ear sound device 610 shown in FIG. 6 and/or the electronic components package 102 shown in FIG. 1. The in-ear sound device 1201 also includes a canal 1203 that can be opened and closed using clamps 1204, according to an embodiment of the invention.

Similar to the discussion of the in-ear sound device 1101 shown in FIG. 11, in practical application, the in-ear sound device 1201 is "squished" between the fingers of the user and inserted into the ear canal 1215 where it expands to conform to the shape of the ear canal 1215. In some embodiments, the in-ear sound device 1201 may be returned to a "squished" position before removing the in-ear sound device 1201 from the ear canal 1215. This may allow the in-ear sound device 1201 to slide out of the ear 1205 for easy removal. In other embodiments, the in-ear sound device 1201 may be in an expanded position, or may be in some intermediate position while the in-ear sound device 1201 is removed from the ear canal.

The body of the in-ear sound device 1201 may be composed of the same materials described with respect to the in-ear sound device 1101 shown in FIG. 11, according to an embodiment of the invention.

Figure 13:
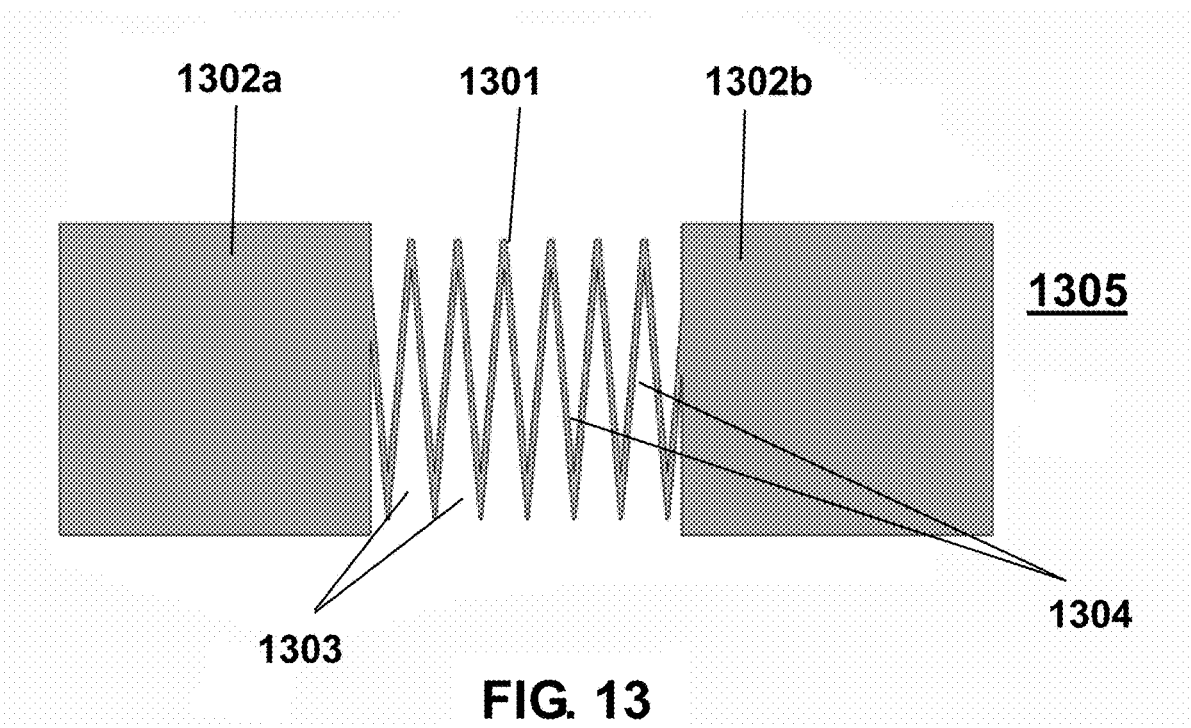
FIG. 13 illustrates an embodiment of the invention that employs stretchable electronics formed on discrete islands 1302a, 1302b of silicon, according to an embodiment of the invention.

FIG. 13 illustrates an embodiment of the invention that employs stretchable electronics by forming the electronics on discrete islands 1302a, 1302b of silicon. FIG. 13 shows a stretchable electronic package 1305 whose discrete electronic islands 1302a, 1302b are connected together using interconnects 1301 having a zigzag pattern 1304, according to an embodiment of the invention. Circuits formed from the stretchable electronics on the discrete islands 130a, 1302b remain electrically coupled via the interconnects 1301 regardless of the amount of strain and/or deformation placed on them by the user and the user's environment.

In embodiments, the discrete islands 1302a, 1302b are discretely operative, may function in a "device islands" arrangement, and are capable of performing the functionality described herein (e.g., the functions shown in FIGS. 1-12 above), or portions thereof. In embodiments, the discrete islands 1302a, 1302b may include integrated circuits, physical sensors (e.g., temperature, pH, light, radiation etc.), biological and/or chemical sensors, amplifiers, ND and D/A converters, optical collectors, electro-mechanical transducers, batteries, piezo-electric actuators, light emitting electronics which include LEDs, and combinations thereof. In other words, the sensors 106a-106z shown in FIG. 1.

Using conventional integrated circuits ("ICs") (e.g., CMOS, on single crystal silicon) enables the utilization of high quality, high performance, and high functioning circuit components that are also already commonly mass-produced using well-known processes. These conventional ICs may provide a range of functionality and generation of data typically superior to that produced by more passive devices.

The discrete islands 1302a, 1302b may range from about, but not limited to, 10-100 μm in size measured on an edge or by diameter, and connecting the discrete islands 1302a, 1302b with one or more extremely stretchable interconnects 1301. The discrete islands 1302a, 1302b may themselves be stretchable or not, according to embodiments of the invention.

The interconnects 1301 have a zigzag pattern 1304 between the discrete islands 1302a, 1302b. The zigzag pattern 1304 provides increased stability and simplicity of manufacture. The zigzag pattern 1304 allows for the twisting, turning, stretching and compressing of the discrete islands 1302a, 1302b while still allowing the stretchable electronic package 1305 and its various components to maintain electric connectivity.

The geometry of the interconnects 1301 makes these interconnects 1301 extremely pliant. Each interconnect 1301 is patterned and etched so that its structural form has width and thickness dimensions that may be of comparable size (such as their ratio or inverse ratio not exceeding about a factor of 10); and may be preferably equal in size. In embodiments, the dimensions may not be greater than about 5 μm (e.g., where both dimensions are about 1 μm or less).

With reference to embodiments of the invention, the term "stretchable," and roots and derivations thereof, when used to modify circuitry or components thereof is meant to encompass circuitry that comprises components having soft or elastic properties capable of being made longer or wider without tearing or breaking, and it is also meant to encompass circuitry having components (whether or not the components themselves are individually stretchable as stated above) that are configured in such a way so as to accommodate and remain functional when applied to a stretchable, inflatable, or otherwise expandable surface.

Stretchable electronic circuitry attaches at least two isolated electronic components (e.g., the discrete islands 1302a, 1302b) to an elastomeric substrate, and arranges an electrical interconnection (e.g., the interconnect 1301) between the components in a boustrophedonic pattern interconnecting the two isolated electronic components with the electrical interconnection. The elastomeric substrate may then be stretched such that the components separate relative to one another, where the electrical interconnection maintains substantially identical electrical performance characteristics during stretching, and where the stretching may extend the separation distance between the electrical components to many times that of the upstretched distance.

In embodiments, the stretching and compressing may be accomplished by fabricating ICs out of thin membrane single crystal semiconductors, which are formed into "islands" that are mechanically and electrically connected by "interconnects," and transferring said ICs onto an elastomeric substrate capable of stretching and compressing. The discrete islands 1302a, 1302b are regions of non-stretchable/compressible ICs, while the interconnects 1301 are regions of material formed in a way to be highly stretchable/compressible, according to an embodiment of the invention. The underlying elastomeric substrate may be more pliant than the discrete islands 1302a, 1302b, so that minimal strain is transferred into the islands 1302a, 1302b while the majority of the strain is transferred to the interconnects 1301, which only contain electrical connections and not less. Each interconnect 1301 attaches one island 1302a to another island 1302b, and is capable of accommodating strain between the two aforementioned islands 1302a, 1302b, including translation, rotation, or a combination of translation with rotation of one island 1302a relative to another 1302b. Even though the interconnects 1301 may be made of a rigid material, they act like weak springs rather than rigid plates or beams. This configuration thereby allows for the making of the extremely stretchable electronics package 1305.

With reference to embodiments of the invention, the term "stretchable", and roots and derivations thereof, when used to modify circuitry or components thereof is meant to encompass circuitry that comprises components having soft or elastic properties capable of being made longer or wider without tearing or breaking, and it is also meant to encompass circuitry having components (whether or not the components themselves are individually stretchable as stated above) that are configured in such a way so as to accommodate and remain functional when applied to a stretchable, inflatable, or otherwise expandable surface. The term "expandable," and roots and derivations thereof, when used to modify circuitry or components thereof is also meant to have the meaning ascribed above. Thus, "stretch" and "expand," and all derivations thereof, may be used interchangeably when referring to embodiments of the invention.

Figure 14:
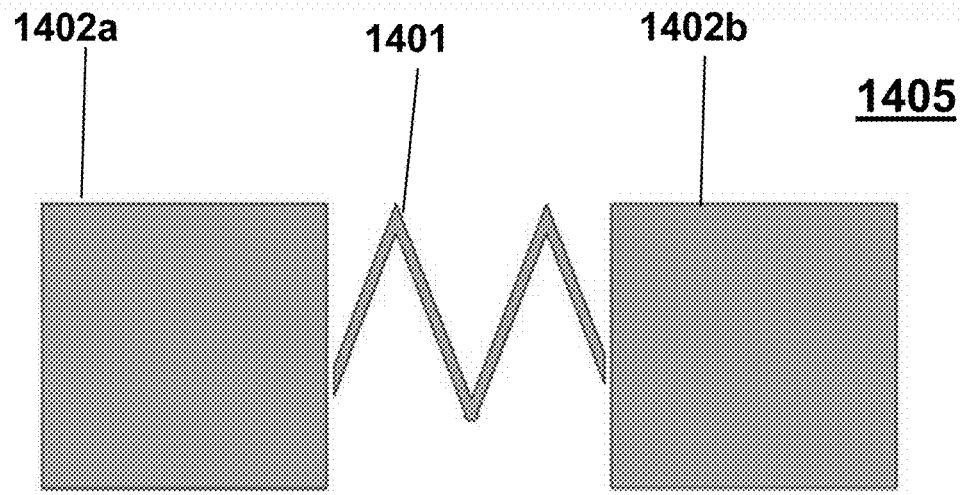
FIG. 14 illustrates an alternative embodiment of the invention that employs stretchable electronics formed on discrete islands 1402a, 1402b of silicon, according to an embodiment of the invention.

FIG. 14 illustrates an alternative embodiment of the invention that employs a stretchable electronic package 1405 comprising discrete islands 1402a, 1402b bound together using a shorter interconnect 1401 than shown in the interconnect 1301 shown in FIG. 13, according to embodiment of the invention.

Figure 15:
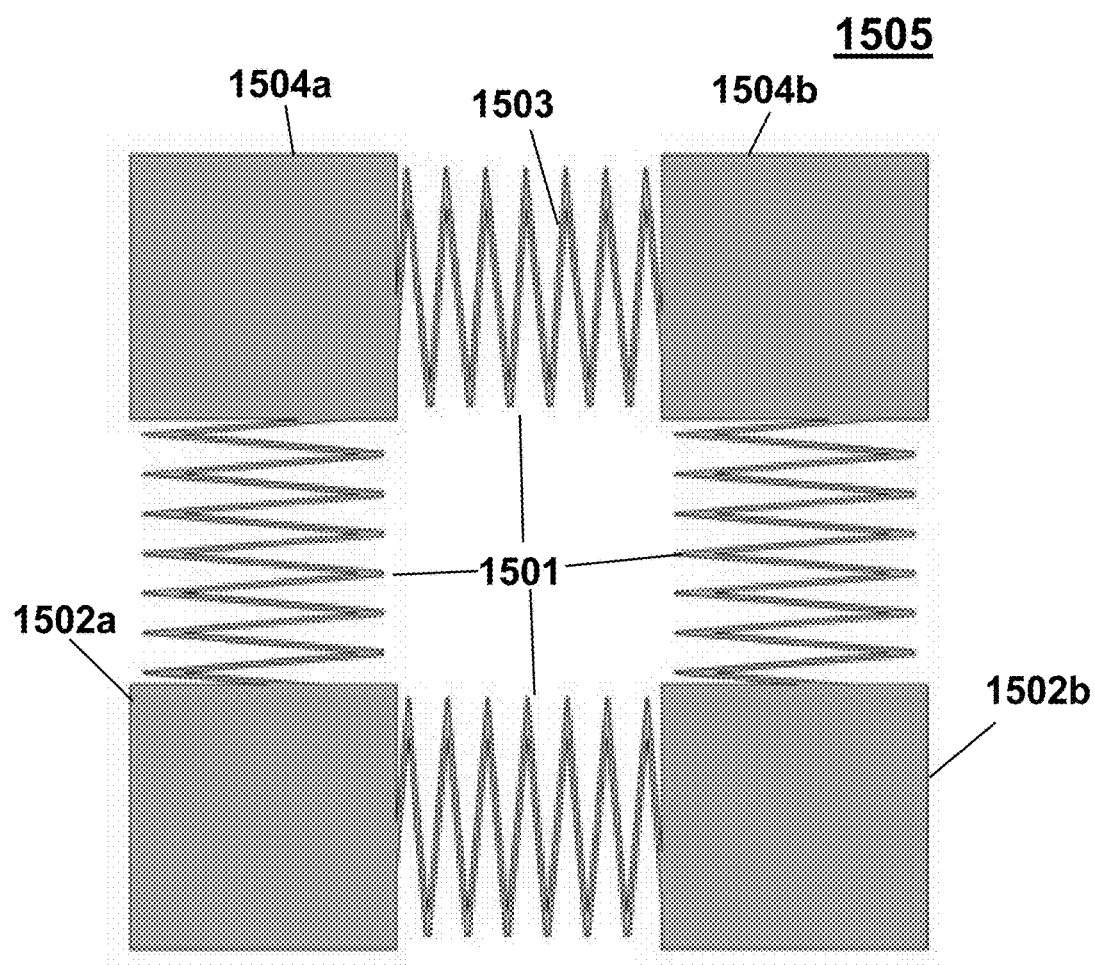
FIG. 15 illustrates an electronics package 1505 comprising discrete islands 1502a, 1502b, 1504a, and 1504b bound together using zigzag interconnects 1501, according to an embodiment of the invention.

FIG. 15 illustrates an electronics package 1505 comprising discrete islands 1502a, 1502b, 1504a, and 1504b bound together using zigzag interconnects 1501, according to an embodiment of the invention. Similar to the discrete islands 1302a, 1302b shown in FIG. 13, the discrete islands 1502a, 1502b, 1504a, and 1504b comprise various electronic components, according to an embodiment of the invention.

The use of interconnects 1501 running in a variety of directions from the islands 1502a, 1502b, 1504a, 1504b allows the islands to be stretched in a variety of directions, according to an embodiment of the invention. The interconnects 1501 may be replaced with or mixed with various other types of interconnects, according to embodiments of the invention.

Figure 16:
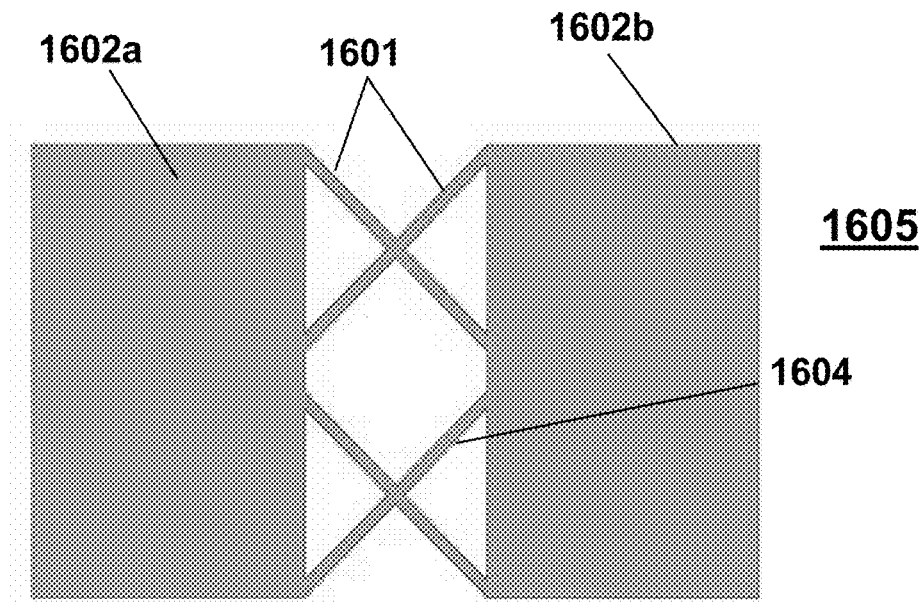
FIG. 16 illustrates an embodiment of the invention that employs a stretchable electronic package 1605 in which the electronics have been formed on discrete islands 1602a, 1602b of silicon bound together using interconnects 1601 having a crisscross or X-pattern 1604, according to an embodiment of the invention.

FIG. 16 illustrates an embodiment of the invention that employs a stretchable electronic package 1605 in which the electronics have been formed on discrete islands 1602a, 1602b of silicon bound together using interconnects 1601 having a crisscross or X-pattern 1604, according to an embodiment of the invention.

In embodiments, the discrete islands 1602a, 1602b are discretely operative, may function in a "device islands" arrangement, and are capable of performing the functionality described herein, or portions thereof. In embodiments, the discrete islands 1602a, 1602b may include integrated circuits (e.g., the electronic component package 102 shown in FIG. 1) and sensors (e.g., the sensors 106a-106z shown in FIG. 1), other electronic components, and combinations thereof.

Figure 17:
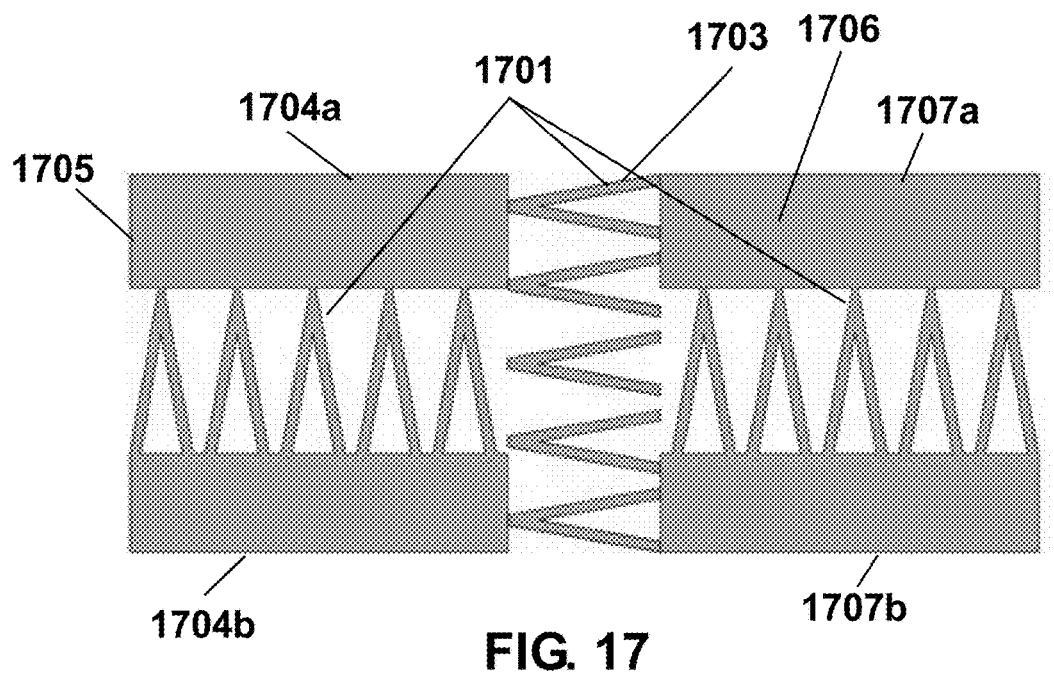
FIG. 17 illustrates an electronics package 1705 bound to another stretchable electronics package 1706 using zigzag interconnects 1703, according to an embodiment of the invention.

FIG. 17 illustrates an electronics package 1705 bound to another stretchable electronics package 1706 using zigzag interconnects 1703. The electronics package 1705 has been formed from electronics located on discrete islands 1704a, 1704b held together using zigzag interconnects 1701. Similarly, the electronics package 1706 has been formed from electronics on discrete islands 1707a, 1707b also held together using zigzag interconnects 1701. The two electronics packages 1705 and 1706 are bound to each other using zigzag interconnects 1703.

The use of interconnects 1701 running in a variety of directions from the islands 1704a, 1704b, 1707a, 1707b allows the islands to be stretched in a variety of directions, according to an embodiment of the invention. The interconnects 1701 may be replaced with or mixed with various other types of interconnects, according to embodiments of the invention.

FIG. 18 illustrates a three-dimensional (3D) printer 1810 that may form an in-ear sound device 1832. In general, 3D printing is an additive part-forming technique that incrementally builds an object by applying a plurality of successive thin material layers. The 3D printer 1810 includes a print head 1812 configured to controllably deposit/bind a stock material onto a substrate. The stock material may comprise an electronic component package 1814 (e.g., the electronic component package 611 shown in FIG. 6) bound to the material 1816 of the earplug (e.g., the deformable body 607 shown in FIG. 6 and/or electronic component package 102 shown in FIG. 1). A motion controller 1818 is configured to controllably translate the print head 1812 within a predefined workspace. The techniques described with respect to FIG. 18 are applicable to a type of 3D printing known as Fused Filament Fabrication. Other types and forms of 3D printers may be used to print the in-ear sound device 1832. The print head 1812 may be configured to receive the material for the electronic component package 1814 from a source such as a spool 1820 or hopper, melt the stock material (e.g., using a resistive heating element 1822), and expel the molten material for the electronic component package 1814 onto the substrate of the ear plug 1816 via a nozzle 1824. In general, the nozzle 1824 may define an orifice 1826 at its distal tip 1828 through which the molten material 1814 may exit the print head 1812.

Once out of the nozzle 1824, the molten material for the electronic component package 1814 may begin cooling, and may re-solidify onto the substrate of the ear plug 1816. Where the molten electronic component package material 1814 is applied over a previously formed material layer 1834 (e.g., a portion of the earplug), the temperature of the molten stock material 1814 may cause localized surface melting to occur in the previous material layer 1834. This localized melting may aid in bonding the newly applied material with the previous layers 1834.

In one embodiment, the print head 1812 may be controlled within a Cartesian coordinate system 1836, where three actuators can each cause a resultant motion of the print head 1812 in a respective orthogonal plane (where convention defines the X-Y plane as a plane parallel to the work surface 1830, and the Z-direction as a dimension orthogonal to the work surface 1830). As material for the electronic component package 1814 is applied to the substrate of the earplug 1816, the thickness 1838 and width of the applied material bead may be a function of the motion 1840 of the print head 1812 relative to the substrate of the earplug 1816, as well as the rate at which the solid stock material of the electronic component package 1814 is fed into the print head 1812. For a constant print head motion 1840 and constant feed rate for the solid stock material for the electronic component package 1814, each applied material bead may have a substantially constant height/thickness 1838 and width.

Some components of the electronic components package 1814 might not be amendable to printing using a 3D printer because of various post-production requirements. For example, speakers (e.g., the speaker 108 shown in FIG. 1) generally require tuning which often requires stretching. Thus, in some embodiments, the in-ear sound device 1832 may be primarily manufactured using the 3D printer 1810 with some additional components, such as a speaker, added at the end of production or at some phase during the product not controlled by the 3D printer 1810 (e.g., added by another device or inserted by hand). This should be relatively simple for the speaker since the speaker is typically located at an end of the in-ear sound device 1832. A fully tuned speaker could be added to the end of the semi-finished in-ear sound device using a mechanical production apparatus, for example.

In embodiments, the in-ear sound device 1832 may be considered disposable and may be intended for single or limited use due to the reduced cost of the device.

Figure 19:
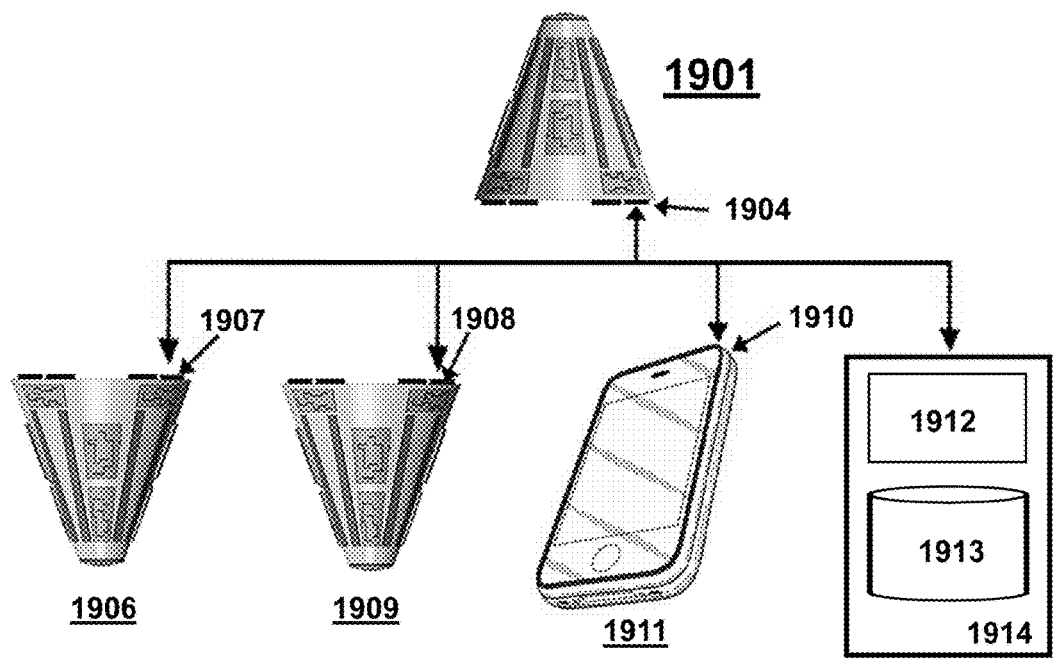
FIG. 19 illustrates an in-ear sound device 1901 communicating wirelessly with other devices 1906, 1909, 1911, and 1914, according to an embodiment of the invention.

FIG. 19 illustrates an in-ear sound device 1901 communicating wirelessly with other devices 1906, 1909, 1911, and 1914, according to an embodiment of the invention.

A communications module 1904 on the in-ear sound device 1901 may be configured to communicate wirelessly with a communication module 1907 on an in-ear sound device 1906 paired with the in-ear sound device 1901. In other words, a user might wear the in-ear sound device 1901 in a left ear, and the in-ear sound device 1906 might be worn in the user's right ear. The in-ear sound device 1901 may communicate wirelessly with the paired in-ear sound device 1906 using a variety of communications protocols, such as NFC communications as discussed above.

The in-ear sound device 1901 may also be in communication with another in-ear sound device 1909 via the communications module 1908 on the in-ear sound device 1909. The communication module 1904 may use a different communication protocol in communicating with the communications module 1908 on the in-ear sound device 1909 than the in-ear sound device 1901 uses with a closely tethered device such as the in-ear sound device 1906.

The in-ear sound device 1901 may also communicate with a transceiver 1910 on a mobile phone 1911. The mobile phone 1911 may be a device such as smartphone. The communications module 1904 may use a different communication protocol than used to communicate with the in-ear sound device 1906 or the in-ear sound device 1909.

The in-ear sound device 1901 may also communicate with a remote data server 1913 located on a remote computing device 1914 via a communication module 1912 associated with the remote data server 1913. The remote data server 1913 may, for example, comprise a server and even a cloud computing device, according to an embodiment of the invention.

The in-ear sound device 1901 may not necessarily be equipped to communicate with all the devices 1906, 1909, 1911, and 1914. The communication module 1904 may be configured for just one type of communication, according to an embodiment of the invention. Similarly, the communication module 1904 may be configured for communications using a series of different communications protocols.

It should be apparent to those skilled in the art that many more modifications of the in-ear sound device besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

While specific embodiments of the invention have been illustrated and described, it will be clear that the invention is not limited to these embodiments only. Embodiments of the invention discussed herein may have generally implied the use of materials from certain named equipment manufacturers; however, the invention may be adapted for use with equipment from other sources and manufacturers. Equipment used in conjunction with the invention may be configured to operate according to conventional protocols (e.g., USB) and/or may be configured to operate according to specialized protocols. Numerous modifications, changes, variations, substitutions and equivalents will be apparent to those skilled in the art without departing from the spirit and scope of the invention as described in the claims. In general, in the following claims, the terms used should not be construed to limit the invention to the specific embodiments disclosed in the specification, but should be construed to include all systems and methods that operate under the claims set forth hereinbelow. Thus, it is intended that the invention covers the modifications and variations of this invention provided they come within the scope of the appended claims and their equivalents.

We claim:

1. A deformable and flexible in-ear sound device, comprising: a deformable and flexible body having a longitudinal axis extending between a distal end and a proximal end; an electronic component package comprising stretchable electronic circuitry, wherein the electronic component package includes a speaker located at the proximal end of the deformable and flexible body and wherein the stretchable electronic circuitry is at least one of embedded in or on the deformable and flexible body at least one sensor in the electronic component package configured to measure a data element; and a processor in the electronic component package configured to analyze the data element and take an action if the data element exceeds a threshold wherein the at least one sensor and the processor are configured to operate as a measurement device that provides one of an alarm, a stop watch, a calendar, and a notification function and wherein the action if the data element exceeds the threshold related to the measurement device comprises sending a sound notification to the speaker; and a communication module in communication with a remote device and wherein the action if the data element exceeds the threshold related to the measurement device further comprises sending a notification to the remote device via the communication module.

2. The deformable and flexible in-ear sound device of claim 1 wherein the stretchable electronic circuitry comprises stretchable interconnects that electrically couple electronic components of the electronic component package, including the processor and the speaker.

3. The deformable and flexible in-ear sound device of claim 2 wherein electronic components of the electronic component package are arranged in a boustrophedonic pattern connected by the stretchable interconnects.

4. The deformable and flexible in-ear sound device of claim 2 wherein the stretchable interconnects connect the electronic components of the electronic component package using one of a zigzag pattern and an X-cross pattern.

5. The deformable and flexible in-ear sound device of claim 2 wherein a plurality of electronic components of the electronic component package are also stretchable.

6. The deformable and flexible in-ear sound device of claim 1 wherein the deformable and flexible body is composed of a material having a Shore A Durometer hardness value between 10 and 30.

7. The deformable and flexible in-ear sound device of claim 1 wherein the deformable and flexible body and the stretchable electronic circuitry are comprised of materials suitable for manufacture in an integral unit by a 3D printer.

8. The deformable and flexible in-ear sound device of claim 1 wherein the deformable and flexible body includes a canal along the longitudinal axis that extends from the distal end to the proximal end, the deformable and flexible in-ear sound device further comprising: a plurality of clamps configured to open and close the canal, wherein opening the canal lowers back pressure in an ear of the user.

9. The deformable and flexible in-ear sound device of claim 1, wherein the electronic component package further comprises the communications module and the processor, wherein the processor: is configured to operate the speaker and the communication module as a headset that receives sound data from the remote device and plays the sound data through the speaker.

10. The deformable and flexible in-ear sound device of claim 9 wherein the processor comprises a CPU.

11. The deformable and flexible in-ear sound device of claim 9 wherein the remote device comprises a portable electronic device and wherein the communication module is configured for short-range communications.

12. The deformable and flexible in-ear sound device of claim 11 wherein the short-range communications comprises the Bluetooth protocol.

13. The deformable and flexible in-ear sound device of claim 11 wherein the portable electronic device comprises a mobile phone.

14. The deformable and flexible in-ear sound device of claim 1, wherein the electronic component package further comprises: a data storage component having stored sound data; wherein the processor has been configured to operate the speaker and the data storage component as a music player that retrieves sound data from the data storage component and plays the sound data through the speaker.

15. The deformable and flexible in-ear sound device of claim 14 wherein the processor comprises a CPU.

16. The deformable and flexible in-ear sound device of claim 1, wherein the electronic component package further comprises: a microphone located at the distal end of the deformable and flexible body and configured to convert sounds external to the deformable and flexible in-ear sound device into an electrical signal; an amplifier configured to increase power of the electrical signal; wherein the processor has been configured to operate the speaker, the microphone, and the amplifier as a hearing device that receives external sounds in the microphone that converts the external sounds to the electrical signal, amplifies the electrical signal in the amplifier, and delivers the electrical signal to the speaker.

17. The deformable and flexible in-ear sound device of claim 16 wherein the processor comprises a CPU.

18. The deformable and flexible in-ear sound device of claim 16, further comprising a digital signal processor, wherein the processor control circuit is configured to operate the digital signal processor.

19. The deformable and flexible in-ear sound device of claim 1, wherein the electronic component package further comprises: a microphone located at the distal end of the deformable and flexible body and configured to convert sounds external to the deformable and flexible in-ear sound device into an electrical signal; wherein the processor has been configured to operate the speaker, the communication module, and the microphone as a two-way communication device that receives sound data from the remote device via the communication module and plays the sound data through the speaker and further configured to receive sound data from the microphone and send the sound data to the remote device from the communication module.

20. The deformable and flexible in-ear sound device of claim 19 wherein the processor comprises a CPU.

21. The deformable and flexible in-ear sound device of claim 19 wherein the remote device comprises another deformable and flexible in-ear sound device and wherein the communication module is configured for short-range communications.

22. The deformable and flexible in-ear sound device of claim 21 wherein the short-range communications comprises at least one of Bluetooth and near-field communication ("NFC").

23. The deformable and flexible in-ear sound device of claim 1 wherein the processor is configured to execute software applications.

24. The deformable and flexible in-ear sound device of claim 23 wherein the electronic component package further comprises a data storage component configured to store software applications for execution by the processor.

25. The deformable and flexible in-ear sound device of claim 23 wherein the communication module is configured to receive data comprising instructions for software applications from the remote device and provide the data to the processor.

26. The deformable and flexible in-ear sound device of claim 1 wherein the electronic component package further comprises: a microphone configured to receive sounds external to the deformable and flexible in-ear sound device; wherein the processor is configured to analyze the received sounds, separate meaningful sounds from ambient noise, and provide the meaningful sounds to the speaker.

27. The deformable and flexible in-ear sound device of claim 1 wherein the communication module is configured to receive data from the remote device using at least one of Bluetooth, Wi-Fi, BLTE, near-field communication, Global System for Mobile Communications (GSM), Code Division Multiple Access-One (cdmaOne), Time Division Multiple Access (TDMA), PDC, Japan Digital Cellular (JDC), Universal Mobile Telecommunications System (UMTS), Code Division Multiple Access-2000 (cdma2000), and Digital Enhanced Cordless Telephony (DECT).

28. The deformable and flexible in-ear sound device of claim 1 wherein the at least one sensor and the processor are arranged to provide a user interface for a user of the deformable and flexible in-ear sound device by receiving instructions from the user and wherein the speaker is configured to deliver operating instructions to the speaker.

29. The deformable and flexible in-ear sound device of claim 1 wherein the at least one sensor is configured as at least one of a thermometer, a pulse rate monitor, a heart rate monitor, a VO2 Max monitor, a pulse oximetry monitor, a respiratory rate monitor, a respiratory monitor, an oxygen consumption monitor, a cardiac efficiency monitor, a heart rate variability monitor, a metabolic rate monitor, a blood pressure monitor, an EEG data monitor, a galvanic skin response monitor, an EKG/ECG monitor, a blood analyte monitor, an ambient temperature monitor, a humidity monitor, a motion detector, a GPS locator, a pressure sensor, an altitude sensor, an accelerometer, a gyroscope, and a magnetometer.

30. The deformable and flexible in-ear sound device of claim 1 further comprising: a microphone configured to receive sound data from a user's voice; a data repository containing identification data related to the user's voice; wherein the processor is configured to analyze the received sound data to determine if it matches the identification data and further configured to take an action if the identification data matches the received sound data.

31. A method for outputting sound to a user's ear by a deformable and flexible in-ear sound device having an electronic component package comprising stretchable electronic circuitry on a deformable and flexible body having a longitudinal axis extending between a distal end and a proximal end, wherein the stretchable electronic circuitry resides on the deformable and flexible body by at least one of embedding the electronic component package in or on the deformable and flexible body, the method comprising: playing audible sounds by a speaker at the proximal end of the deformable and flexible body to the user's ear; measuring a data element by at least one sensor in the electronic component package; analyzing the data element by a processor in the electronic component package configured to take an action if the data element exceeds a threshold, wherein the at least one sensor and the processor are configured to operate as a measurement device that provides one of an alarm, a stop watch, a calendar, and a notification function; sending a sound notification to the speaker if the data element exceeds the threshold related to the measurement device; communicating with a remote device using a communication module; and sending a notification to the remote device via the communication module if the data element exceeds the threshold related to the measurement device.

32. The method of claim 31, further comprising: electrically coupling stretchable interconnects in the stretchable electronic circuitry.

33. The method of claim 31, further comprising: arranging electronic components of the electronic component package in a boustrophedonic pattern connected by the stretchable interconnects.

34. The method of claim 31, further comprising: connecting the stretchable interconnects to the electronic components of the electronic component package using one of a zigzag pattern and an X-cross pattern.

35. The method of claim 31 wherein the deformable and flexible body comprises a material having a Shore A Durometer hardness value between 10 and 30.

36. The method of claim 31 wherein placing the electronic component package on the deformable and flexible body comprises printing the electronic component package and the deformable and flexible body as an integral unit on a 3D printer.

37. The method of claim 31 wherein the deformable and flexible body includes a canal along the longitudinal axis that extends from the distal end to the proximal end, the deformable and flexible in-ear sound device further comprising: configuring a plurality of clamps to open and close the canal, wherein opening the canal lowers back pressure in an ear of the user.

38. The method of claim 31 further comprising: configuring a communication module in the electronic component package for communication with a remote device; and configuring the processor residing in the electronic component package to operate the speaker and the communication module as a headset that receives sound data from the remote device and plays the sound data through the speaker.

39. The method of claim 38 wherein the remote device comprises a portable electronic device, the method further comprising configuring the communication module for short-range communications.

40. The method of claim 39 wherein the short-range communications comprises the Bluetooth protocol.

41. The method of claim 39 wherein the portable electronic device comprises a mobile phone.

42. The method of claim 31, further comprising: storing data in a data storage component in the electrical component package; and configuring the processor to operate the speaker and the data storage component as a music player that retrieves sound data from the data storage component and plays the sound data through the speaker.

43. The method of claim 31, further comprising: converting sounds external to the deformable and flexible in-ear sound device by a microphone located at the distal end of the deformable and flexible body into an electrical signal; increasing power of the electrical signal by an amplifier located in the electronic component package; and operating the processor as a hearing device, wherein the processor control circuit controls the speaker, the microphone, and the amplifier to receive external sounds in the microphone, converts the external sounds to the electrical signal, amplifies the electrical signal in the amplifier, and delivers the electrical signal to the speaker.

44. The method of claim 43, further comprising a digital signal processor controlled by the processor.

45. The method of claim 31, further comprises: converting sounds external to the deformable and flexible in-ear sound device into an electrical signal by a microphone located at the distal end of the deformable and flexible body; and operating the processor as a two-way communication device by controlling the speaker, the communication module, and the microphone to receive sound data from the remote device via the communication module and play the sound data through the speaker and further configured to receive sound data from the microphone and send the sound data to the remote device from the communication module.

46. The method of claim 45 wherein the remote device comprises another deformable and flexible in-ear sound device, the method further comprising configuring the communication module for short-range communications.

47. The method of claim 46 wherein the short-range communications comprises at least one of Bluetooth and near-field communication ("NFC").

48. The method of claim 31, further comprising: executing a software application in the processor located in the electronic component package.

49. The method of claim 31, further comprising: receiving in a microphone sounds external to the deformable and flexible in-ear sound device; analyzing the received sounds in the processor; separating meaningful sounds from ambient noise in the received sounds; and providing the meaningful sounds to the speaker.

50. The method of claim 31 further comprising: receiving data from the remote device by the communication module in the electronic component package using at least one of Bluetooth, Wi-Fi, BLTE, near-field communication, Global System for Mobile Communications (GSM), Code Division Multiple Access-One (cdmaOne), Time Division Multiple Access (TDMA), PDC, Japan Digital Cellular (JDC), Universal Mobile Telecommunications System (UMTS), Code Division Multiple Access-2000 (cdma2000), and Digital Enhanced Cordless Telephony (DECT).

51. The method of claim 31 wherein the at least one sensor and the processor are arranged to provide a user interface for a user of the deformable and flexible in-ear sound device, comprising: receiving instruction input from the user by the at least one sensor; analyzing the received instruction input by a processor in the electronic component package; and delivering operating instructions to the user by the speaker.

52. The method of claim 31 wherein the at least one sensor is configured as at least one of a thermometer, a pulse rate monitor, a heart rate monitor, a V02 Max monitor, a pulse oximetry monitor, a respiratory rate monitor, a respiratory monitor, an oxygen consumption monitor, a cardiac efficiency monitor, a heart rate variability monitor, a metabolic rate monitor, a blood pressure monitor, an EEG data monitor, a galvanic skin response monitor, an EKG/ECG monitor, a blood analyte monitor, an ambient temperature monitor, a humidity monitor, a motion detector, a GPS locator, a pressure sensor, an altitude sensor, an accelerometer, a gyroscope, and a magnetometer.

53. The method of claim 31 further comprising: receiving sound data related to from a user's voice by a microphone in the electronics component package; and analyzing the received sound data by the processor residing in the electronics component package to determine if the received data matches identification data related to the user's voice, wherein the identification data is stored in a data component in the electronics component package; and taking an action by the processor if the identification data matches the received sound data.

* * * * *